United States Patent
Ting et al.

(10) Patent No.: US 7,559,902 B2
(45) Date of Patent: Jul. 14, 2009

(54) PHYSIOLOGICAL MONITORING GARMENT

(75) Inventors: Joseph Ting, Acton, MA (US); Brian Farrell, Quincy, MA (US); Jeremy Bowman, Arlington, MA (US)

(73) Assignee: Foster-Miller, Inc., Waltham, MA (US)

( * ) Notice: Subject to any disclaimer, the term of this patent is extended or adjusted under 35 U.S.C. 154(b) by 843 days.

(21) Appl. No.: 10/922,336

(22) Filed: Aug. 20, 2004

(65) Prior Publication Data
US 2005/0054941 A1 Mar. 10, 2005

Related U.S. Application Data

(60) Provisional application No. 60/497,423, filed on Aug. 22, 2003.

(51) Int. Cl.
*A61B 5/08* (2006.01)
(52) U.S. Cl. .................. 600/529; 600/300; 600/388
(58) Field of Classification Search .......... 600/300, 600/529
See application file for complete search history.

(56) References Cited

U.S. PATENT DOCUMENTS

| | | | |
|---|---|---|---|
| 2,021,111 A | 11/1935 | Wheat | |
| 2,953,970 A | 9/1960 | Maynard | |
| 2,963,535 A | 12/1960 | Wegener et al. | |
| 2,963,538 A | 12/1960 | Dahlgren | |
| 2,997,521 A | 8/1961 | Dahlgren | |
| 3,086,071 A | 4/1963 | Preston | |
| 3,229,030 A | 1/1966 | Baermann | |
| 3,247,755 A | 4/1966 | Siegmund | |
| 3,288,175 A | 11/1966 | Valko | |
| 3,371,250 A | 2/1968 | Ross et al. | |
| 3,414,666 A | 12/1968 | Doundoulakis et al. | |
| 3,447,120 A | 5/1969 | Rask et al. | |
| 3,473,872 A | 10/1969 | Okamura | |
| 3,476,870 A | 11/1969 | Ross | |
| 3,479,565 A | 11/1969 | Ross et al. | |
| 3,495,025 A | 2/1970 | Ross | |
| 3,507,321 A | 4/1970 | Palma | |

(Continued)

FOREIGN PATENT DOCUMENTS

DE 103 06 953 A1 10/2003

(Continued)

OTHER PUBLICATIONS

Gemperle, Francine, Kasabach, Chris, Stivoric, John, Bauer, Malcolm, and Martin, Richard, *Design for Wearability*, Institute for Complex Engineered Systems, Carnegie Mellon University, Pittsburgh, PA, http://www.ices.cmu.edu/design/wearability, 1998 (7 pages).

(Continued)

*Primary Examiner*—Patricia Mallari
*Assistant Examiner*—Karen E Toth
(74) *Attorney, Agent, or Firm*—Iandiorio Teska & Coleman

(57) ABSTRACT

A physiological monitoring garment includes first and second elastic fabric portions. An elongate stretchable textile data/power bus is disposed between the first and second elastic fabric portions. The elongate stretchable textile data/power bus includes a plurality of integral conductors, woven, knitted, or braided along the length thereof. One or more sensors are connected to the elongate stretchable textile data/power bus.

28 Claims, 21 Drawing Sheets

U.S. PATENT DOCUMENTS

| | | |
|---|---|---|
| 3,551,585 A | 12/1970 | Smart et al. |
| 3,627,903 A | 12/1971 | Plummer |
| 3,631,298 A | 12/1971 | Davis |
| 3,654,380 A | 4/1972 | Tatum et al. |
| 3,700,538 A | 10/1972 | Kennedy |
| 3,711,627 A | 1/1973 | Maringulov |
| 3,778,331 A | 12/1973 | Scharf |
| 3,878,316 A | 4/1975 | Groff |
| 3,882,846 A | 5/1975 | Fletcher et al. |
| 3,891,011 A | 6/1975 | Tisdale et al. |
| 3,909,508 A | 9/1975 | Ross |
| 3,926,360 A | 12/1975 | Moister, Jr. |
| 3,984,622 A | 10/1976 | Ross |
| 4,031,284 A | 6/1977 | Ingraham |
| 4,034,150 A | 7/1977 | Burnett, III |
| 4,035,694 A | 7/1977 | Barton et al. |
| 4,095,042 A | 6/1978 | Ross |
| 4,103,102 A | 7/1978 | Klein |
| 4,106,677 A | 8/1978 | Helmso et al. |
| 4,111,510 A | 9/1978 | Zurcher |
| 4,143,236 A | 3/1979 | Ross et al. |
| 4,145,030 A | 3/1979 | Ingraham |
| 4,150,464 A | 4/1979 | Tracy |
| 4,158,103 A | 6/1979 | Danilin et al. |
| 4,158,104 A | 6/1979 | Ross |
| 4,159,394 A | 6/1979 | Ross |
| 4,171,555 A | 10/1979 | Bakker et al. |
| 4,191,800 A | 3/1980 | Holtzman |
| 4,196,355 A | 4/1980 | Maine |
| 4,227,520 A | 10/1980 | Lord |
| 4,229,615 A | 10/1980 | Orr, Jr. et al. |
| 4,249,267 A | 2/1981 | Voss |
| 4,254,951 A | 3/1981 | DeLaney |
| 4,281,211 A | 7/1981 | Tatum et al. |
| 4,281,237 A | 7/1981 | Berenson |
| 4,370,658 A | 1/1983 | Hill |
| 4,373,534 A | 2/1983 | Watson |
| 4,430,384 A | 2/1984 | George |
| 4,442,314 A | 4/1984 | Piper |
| 4,452,847 A | 6/1984 | Siemon |
| 4,460,803 A | 7/1984 | Piper |
| 4,463,323 A | 7/1984 | Piper |
| 4,504,696 A | 3/1985 | Piper |
| 4,513,055 A | 4/1985 | Leibowitz |
| 4,527,135 A | 7/1985 | Piper |
| 4,550,411 A | 10/1985 | Stonestreet et al. |
| 4,559,411 A | 12/1985 | Piper |
| 4,572,197 A | 2/1986 | Moore et al. |
| 4,590,623 A | 5/1986 | Kitchman |
| 4,658,089 A | 4/1987 | Guzy et al. |
| 4,670,351 A | 6/1987 | Keane et al. |
| 4,682,828 A | 7/1987 | Piper et al. |
| 4,684,762 A | 8/1987 | Gladfelter |
| 4,709,397 A | 11/1987 | Voshall et al. |
| 4,712,298 A | 12/1987 | Mondor, III |
| 4,723,925 A | 2/1988 | Orr, Jr. et al. |
| 4,735,847 A | 4/1988 | Fujiwara et al. |
| 4,741,707 A | 5/1988 | Mondor, III |
| 4,746,769 A | 5/1988 | Piper |
| 4,753,088 A | 6/1988 | Harrison et al. |
| 4,761,005 A | 8/1988 | French et al. |
| 4,774,434 A | 9/1988 | Bennion |
| 4,803,096 A | 2/1989 | Kuhn et al. |
| 4,804,806 A | 2/1989 | Orr, Jr. et al. |
| 4,807,640 A | 2/1989 | Watson et al. |
| 4,808,771 A | 2/1989 | Orr, Jr. |
| 4,814,585 A | 3/1989 | Klein |
| 4,815,473 A | 3/1989 | Watson et al. |
| 4,817,625 A | 4/1989 | Miles |
| 4,827,943 A | 5/1989 | Bornn et al. |
| 4,851,613 A | 7/1989 | Jacques |
| 4,854,446 A | 8/1989 | Strader |
| 4,856,837 A | 8/1989 | Hammersla, Jr. |
| 4,868,565 A | 9/1989 | Mettes et al. |
| 4,875,144 A | 10/1989 | Wainwright |
| 4,877,646 A | 10/1989 | Kuhn et al. |
| 4,910,358 A | 3/1990 | Mittelbusher |
| 4,912,611 A | 3/1990 | Lyle |
| 4,913,978 A | 4/1990 | Klotz et al. |
| 4,930,517 A | 6/1990 | Cohen et al. |
| 4,948,951 A | 8/1990 | Balzano |
| 4,960,118 A | 10/1990 | Pennock |
| 4,983,452 A | 1/1991 | Daimon et al. |
| 4,992,335 A | 2/1991 | Guerra et al. |
| 5,008,517 A | 4/1991 | Brekkestran et al. |
| 5,032,705 A | 7/1991 | Batcheller et al. |
| 5,047,788 A | 9/1991 | Gillard |
| 5,073,984 A | 12/1991 | Tone et al. |
| 5,076,801 A * | 12/1991 | Schroll ........................ 439/404 |
| 5,089,669 A | 2/1992 | Piper et al. |
| 5,095,628 A | 3/1992 | McKenney et al. |
| 5,103,504 A | 4/1992 | Dordevic |
| 5,104,726 A | 4/1992 | Ross |
| 5,119,020 A | 6/1992 | Massey et al. |
| 5,126,920 A | 6/1992 | Cardashian et al. |
| 5,140,131 A | 8/1992 | Macher et al. |
| 5,191,893 A | 3/1993 | Reiten |
| 5,203,717 A | 4/1993 | Beck et al. |
| 5,241,300 A | 8/1993 | Buschmann |
| 5,259,792 A | 11/1993 | Beck et al. |
| 5,277,617 A | 1/1994 | Shasteen |
| 5,295,490 A | 3/1994 | Dodakian |
| 5,301,678 A | 4/1994 | Watson et al. |
| 5,316,830 A | 5/1994 | Adams, Jr. et al. |
| 5,318,845 A | 6/1994 | Tanaka et al. |
| 5,331,115 A | 7/1994 | Ysbrand |
| 5,332,869 A | 7/1994 | Hagiwara |
| 5,342,204 A | 8/1994 | Och |
| 5,357,593 A | 10/1994 | Bossler |
| 5,362,656 A | 11/1994 | McMahon |
| 5,371,326 A | 12/1994 | Clearwaters-Dreager et al. |
| 5,373,103 A | 12/1994 | Orr, Jr. et al. |
| 5,380,954 A | 1/1995 | Orr, Jr. |
| 5,387,113 A | 2/1995 | Dickerson et al. |
| 5,393,928 A | 2/1995 | Cribb et al. |
| 5,457,610 A | 10/1995 | Bernardoni et al. |
| 5,499,927 A | 3/1996 | Ohno et al. |
| 5,502,631 A | 3/1996 | Adachi |
| 5,523,528 A | 6/1996 | Bese et al. |
| 5,531,405 A | 7/1996 | Goldberg |
| 5,532,429 A | 7/1996 | Dickerson et al. |
| 5,538,781 A | 7/1996 | Rao et al. |
| 5,543,585 A | 8/1996 | Booth et al. |
| 5,600,098 A | 2/1997 | Kazaks |
| 5,674,752 A | 10/1997 | Buckley et al. |
| 5,680,681 A | 10/1997 | Fuss |
| 5,691,062 A | 11/1997 | Shalaby et al. |
| 5,701,370 A | 12/1997 | Muhs et al. |
| 5,730,145 A | 3/1998 | Defares et al. |
| 5,747,101 A | 5/1998 | Booth et al. |
| 5,749,365 A * | 5/1998 | Magill ........................ 600/484 |
| 5,760,340 A | 6/1998 | Orr, Jr. et al. |
| 5,763,058 A | 6/1998 | Isen et al. |
| 5,773,762 A | 6/1998 | Orr, Jr. et al. |
| 5,774,341 A | 6/1998 | Urbish et al. |
| 5,786,977 A | 7/1998 | Cohen |
| 5,788,528 A | 8/1998 | Orr, Jr. et al. |
| 5,802,607 A | 9/1998 | Triplette |
| 5,824,996 A | 10/1998 | Kochman et al. |
| 5,829,987 A | 11/1998 | Fritsch et al. |
| 5,832,296 A | 11/1998 | Wang et al. |
| 5,834,693 A | 11/1998 | Waddell et al. |
| 5,837,624 A | 11/1998 | Sakaguchi et al. |
| 5,876,430 A | 3/1999 | Shoberg et al. |

| | | |
|---|---|---|
| 5,883,364 A | 3/1999 | Frei et al. |
| 5,906,004 A | 5/1999 | Lebby et al. |
| 5,911,595 A | 6/1999 | Orr, Jr. et al. |
| 5,912,653 A | 6/1999 | Fitch |
| 5,913,830 A | 6/1999 | Miles |
| 5,914,585 A | 6/1999 | Grabon |
| 5,914,660 A | 6/1999 | Mesibov et al. |
| 5,919,141 A | 7/1999 | Money et al. |
| 5,926,144 A | 7/1999 | Bolanos et al. |
| 5,928,157 A | 7/1999 | O'Dwyer |
| 5,931,764 A | 8/1999 | Freeman et al. |
| 5,970,921 A | 10/1999 | Fulton |
| 5,989,120 A | 11/1999 | Truchsess |
| 5,995,077 A | 11/1999 | Wilcox et al. |
| 5,997,983 A | 12/1999 | Caron et al. |
| 6,023,372 A | 2/2000 | Spitzer et al. |
| 6,024,575 A | 2/2000 | Ulrich |
| 6,026,512 A | 2/2000 | Banks |
| 6,047,203 A | 4/2000 | Sackner et al. |
| 6,080,690 A | 6/2000 | Lebby et al. |
| 6,083,156 A | 7/2000 | Lisiecki |
| 6,097,607 A | 8/2000 | Carroll et al. |
| 6,105,624 A | 8/2000 | Wildeman et al. |
| 6,117,554 A | 9/2000 | Shalaby et al. |
| 6,121,171 A | 9/2000 | Takahashi et al. |
| 6,121,547 A | 9/2000 | Harada |
| 6,126,572 A | 10/2000 | Smith |
| 6,128,004 A | 10/2000 | McDowall et al. |
| 6,145,551 A | 11/2000 | Jayaraman et al. |
| 6,210,771 B1 * | 4/2001 | Post et al. .................... 428/100 |
| 6,231,516 B1 | 5/2001 | Keilman et al. |
| 6,253,099 B1 | 6/2001 | Oskin et al. |
| 6,254,548 B1 * | 7/2001 | Ishikawa et al. ............. 600/549 |
| 6,254,551 B1 | 7/2001 | Varis |
| 6,270,466 B1 | 8/2001 | Weinstein et al. |
| 6,277,080 B1 | 8/2001 | Nissila et al. |
| 6,295,466 B1 * | 9/2001 | Ishikawa et al. ............. 600/509 |
| 6,315,009 B1 | 11/2001 | Jayaraman et al. |
| 6,324,053 B1 | 11/2001 | Kamijo |
| 6,325,066 B1 | 12/2001 | Hughes et al. |
| 6,341,504 B1 | 1/2002 | Istook |
| 6,341,550 B1 | 1/2002 | White |
| 6,350,129 B1 | 2/2002 | Gorlick |
| 6,381,482 B1 * | 4/2002 | Jayaraman et al. .......... 600/388 |
| 6,385,473 B1 | 5/2002 | Haines et al. |
| 6,413,225 B1 | 7/2002 | Sackner et al. |
| 6,416,471 B1 | 7/2002 | Kumar et al. |
| 6,420,008 B1 | 7/2002 | Lewis et al. |
| 6,445,940 B1 * | 9/2002 | Gevins et al. ................ 600/382 |
| 6,461,307 B1 | 10/2002 | Kristbjarnarson et al. |
| 6,463,310 B1 | 10/2002 | Swedlow et al. |
| 6,474,367 B1 | 11/2002 | Jayaraman et al. |
| 6,493,933 B1 | 12/2002 | Post et al. |
| 6,494,829 B1 | 12/2002 | New, Jr. et al. |
| 6,496,695 B1 | 12/2002 | Kouji et al. |
| 6,522,531 B1 | 2/2003 | Quintana et al. |
| 6,527,711 B1 | 3/2003 | Stivoric et al. |
| 6,551,252 B2 | 4/2003 | Sackner et al. |
| 6,561,987 B2 | 5/2003 | Pail |
| 6,677,858 B1 | 1/2004 | Faris et al. |
| 6,687,523 B1 * | 2/2004 | Jayaramen et al. .......... 600/388 |
| 6,727,197 B1 * | 4/2004 | Wilson et al. ................ 442/301 |
| 6,729,025 B2 | 5/2004 | Farrell et al. |
| 6,767,218 B2 | 7/2004 | Marmaropoulos |
| 6,785,144 B1 | 8/2004 | Akram |
| 6,936,011 B2 | 8/2005 | Sheldon |
| 6,941,775 B2 * | 9/2005 | Sharma ........................ 66/202 |
| 6,970,731 B1 | 11/2005 | Jayaraman et al. |
| 7,020,508 B2 | 3/2006 | Stivoric et al. |
| 7,041,062 B2 | 5/2006 | Friedrichs et al. |
| 7,076,291 B2 | 7/2006 | Pulkkinen et al. |
| 7,319,895 B2 * | 1/2008 | Klefstad-Sillonville et al. .. 600/388 |
| 2002/0032388 A1 | 3/2002 | Kristbjarnarson et al. |
| 2002/0044059 A1 | 4/2002 | Reeder et al. |
| 2002/0107451 A1 | 8/2002 | Pulkkinen et al. |
| 2003/0139680 A1 | 7/2003 | Sheldon |
| 2004/0092186 A1 | 5/2004 | Wilson-Nguyen et al. |
| 2004/0097823 A1 | 5/2004 | Friedrichs et al. |
| 2004/0209396 A1 * | 10/2004 | Krulevitch et al. .......... 438/106 |
| 2004/0224138 A1 * | 11/2004 | Farrell et al. ................. 428/209 |
| 2005/0119586 A1 | 6/2005 | Coyle et al. |
| 2005/0240087 A1 | 10/2005 | Keenan et al. |
| 2006/0009697 A1 | 1/2006 | Banet et al. |
| 2006/0036142 A1 | 2/2006 | Brister et al. |
| 2006/0117805 A1 | 6/2006 | Valentine et al. |

FOREIGN PATENT DOCUMENTS

| | | |
|---|---|---|
| EP | 0 320 901 A2 | 6/1989 |
| EP | 1 064 963 A1 | 1/2001 |
| EP | 1 077 044 A1 | 2/2001 |
| EP | 1 164 815 A1 | 12/2001 |
| EP | 1 234 903 A1 | 8/2002 |
| EP | 1 328 137 A2 | 7/2003 |
| EP | 1 330 964 A2 | 7/2003 |
| EP | 1 339 259 A1 | 8/2003 |
| EP | 1 444 907 A1 | 8/2004 |
| EP | 1 269 502 B1 | 6/2005 |
| EP | 1 021 064 B1 | 9/2005 |
| EP | 1 049 354 B1 | 12/2005 |
| EP | 1 201 806 B1 | 12/2005 |
| FR | 2 836 050 A1 | 8/2003 |
| FR | 2858758 A2 * | 8/2003 |
| GB | 2 143 135 A | 2/1985 |
| GB | 2 331 631 A | 2/1999 |
| GB | 2 336 514 A | 10/1999 |
| GB | 2 378 054 A | 1/2003 |
| GB | 2 385 277 A | 8/2003 |
| GB | 2 386 339 A | 9/2003 |
| GB | 2 396 256 A | 6/2004 |
| WO | WO 98/20200 | 5/1998 |
| WO | WO 99/19019 | 4/1999 |
| WO | WO 00/25193 | 5/2000 |
| WO | WO 01/78577 A2 | 10/2001 |
| WO | WO 01/88935 | 11/2001 |
| WO | WO 02/07816 | 1/2002 |
| WO | WO 02/045538 A2 | 6/2002 |
| WO | WO 02/060370 A2 | 8/2002 |
| WO | WO 02/087929 A1 | 11/2002 |
| WO | WO 02/095839 A2 | 11/2002 |
| WO | WO 03/039417 A2 | 5/2003 |
| WO | WO 03/052541 A2 | 6/2003 |
| WO | WO 03/072861 A1 | 9/2003 |
| WO | WO 03/094717 A1 | 11/2003 |
| WO | WO 2004/053638 A2 | 6/2004 |
| WO | WO 2004/064108 A2 | 7/2004 |
| WO | WO 2004/091503 A2 | 10/2004 |
| WO | WO 2004/098703 A2 | 11/2004 |
| WO | WO 2004/107831 A2 | 12/2004 |
| WO | WO 2004/114401 A2 | 12/2004 |
| WO | WO 2005/000052 A2 | 1/2005 |
| WO | WO 2005/011415 A1 | 2/2005 |
| WO | WO 2005/013738 A2 | 2/2005 |

OTHER PUBLICATIONS

Harper Charles A., *Handbook of Plastics, Elastomers, and Composites*, Third Edition, McGraw-Hill, New York, 1996, pp. 6.14-6.19.

"Wearable Sensor Badge & Sensor Jacket for Context Awareness", Farringdon et al., Philips Research Laboratories, Surrey, U.K., 1999 IEE, pp. 107-113.

"Electric Suspenders: A Fabric Power Bus and Data Network for Wearable Digital Devices", Michael M. Gorlick, The Aerospace Corporation, El Segundo, California, 1999 IEEE, pp. 114-121.

"E-broidery: Design and Fabrication of Textile-based Computing", by E.R. Post et al., IBM Systems Journal, vol. 39, Nos. 3&4, 2000, pp. 840-860.

"Intrabody Buses for Data and Power", E. Rhemi Post et al., MIT Media Laboratory, 1997 IEE, pp. 52-55.

Neuman, Michael R., *Biopotential Electrodes*, The Biomedical Engineering Handbook, vol. I, edited by Joseph D. Bronzino, CRC Press, Boca Raton, FL, 2000, pp. 48-1-48-12.

Post, E. Rehmi and Maggie Orth, *Smart Fabric, or "Wearable Clothing,"* the MIT Media Laboratory, pp. 167-168 of the Digest of Papers of the First IEEE International Symposium on Wearable Computers, Oct. 13-14, 1997 held in Cambridge, Massachusetts.

Post, E. Rehmi and Maggie Orth, *Smart Fabric, or Washable Computing* the MIT Media Laboratory, Digest of Papers of the First IEEE International Symposium on Wearable Computers, Oct. 13-14, 1997 held in Cambridge, Massachusetts, 4 pages.

\* cited by examiner

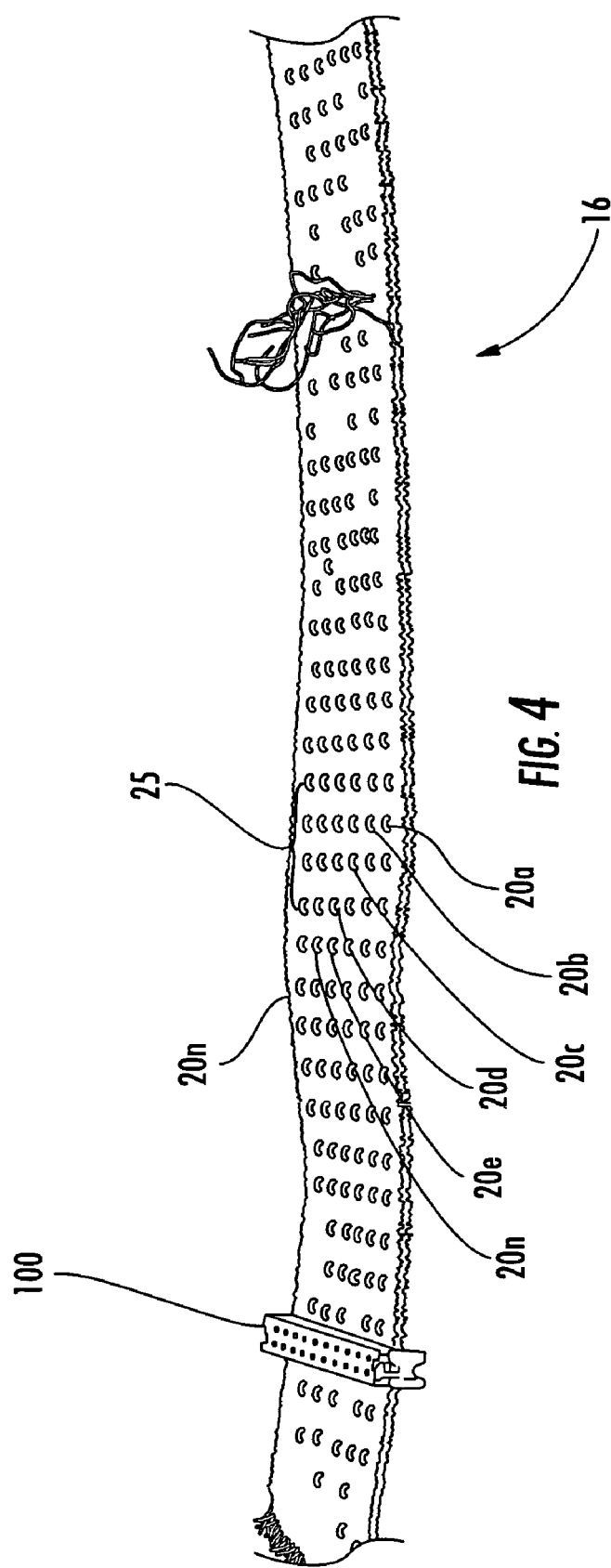

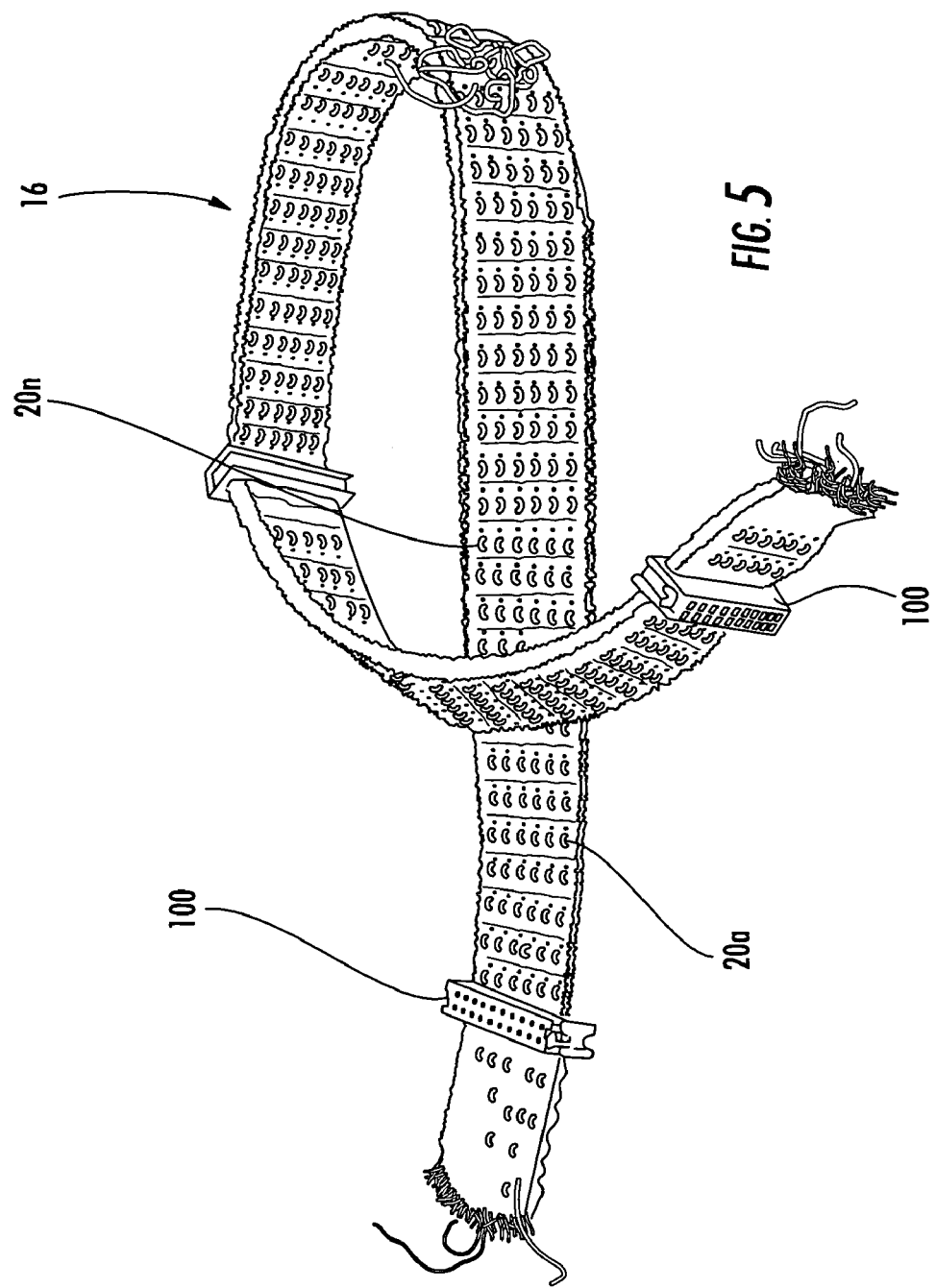

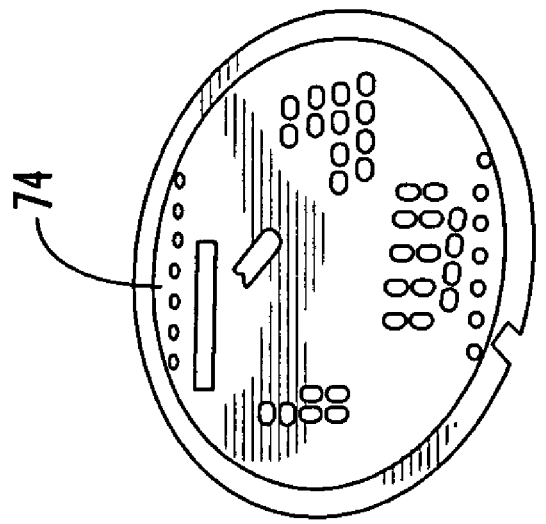
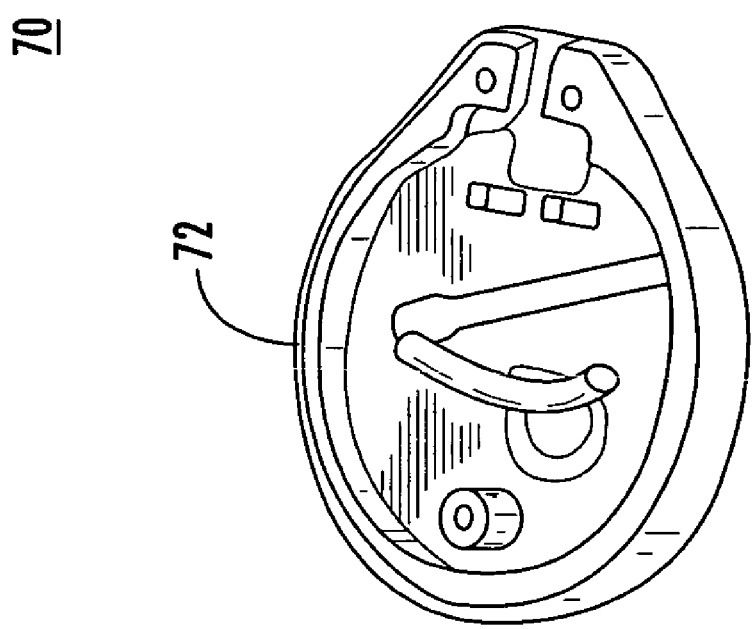
FIG. 12
(PRIOR ART)

PHYSIOLOGICAL MONITORING GARMENT

RELATED APPLICATIONS

This application claims the benefit of U.S. Provisional Application Ser. No. 60/497,423 filed Aug. 22, 2003, which is incorporated herein by reference.

GOVERNMENT RIGHTS

This invention was made with U.S. Government support under Contract No. Contract No. DAMD17-03-C-0022 awarded by the U.S. Army Medical Material Command. The Government may have certain rights in the subject invention.

FIELD OF THE INVENTION

This invention relates to "wearable electronics", "wearable computers", "smart fabrics" and the like and more particularly a physiological monitoring garment including at least an integrated data/power bus. This invention also relates to a respiration monitoring device and sensors useful in connection with the physiological monitoring garment or other physiological sensor systems.

BACKGROUND OF THE INVENTION

The idea of "wearable computers" and electronic circuits built entirely out of textiles to distribute data and power and designed to perform functions such as touch sensing was first fully described in a disclosure called "Smart Fabric, or Washable Computing" by E. Rehmi Post and Maggie Orth of the MIT Media Laboratory available on the Internet at http://www.media.mit.edu/%7EREHMI/fabric/index.html and also on pp. 167-168 of the Digest of Papers of the First IEEE International Symposium on Wearable Computers, Oct. 13-14, 1997 held in Cambridge, Mass.

Prior to the applicant's invention described herein, electrical or electronic components were sometimes fastened to articles of clothing or placed in pouches or pockets. Individual wires between these components were then fastened to the outside of the clothing or disposed partially or wholly in seams and the like. In this way, a soldier could "wear" a radio and a computer and/or global positioning satellite system. Consumers, in turn, could, for example, "wear" a cellular telephone connected to a headset or a speaker and/or microphone located on the collar of a jacket.

The problem with this design is that the wires are separate from the textile material of the clothing. As a result, the wires are unsightly and uncomfortable, do not wear well, can catch and tangle on objects, reduce mobility, add weight, are not washable, and are not resistant to corrosion. In general, such a design is not very robust.

Therefore, those skilled in the art sought to integrate the electronic circuits and data and power conductors within the textile of the articles of clothing themselves. See the MIT disclosure referred to above and incorporated herein by this reference. In the MIT reference, metallic yarn forms the weft of the fabric and, running in the other direction, plain silk thread forms the warp of the fabric. Surface mount light emitting diodes (LED's), crystal piezo transducers, and other surface mount components are then soldered directly onto the metallic yarn.

But, since the metallic yarn only runs in one direction, communications and interconnections between the electronic devices can only take place in that direction. Worse, the individual metallic yarns which do not electrically interconnect two components must be cut to provide electrical isolation for the individual metallic yarns which do electrically interconnect two components. This design thus raises serious design concerns, namely manufacturability, shielding, and electrical interference. Moreover, the fabric including the soldered-on electronic components is delicate, cannot be washed, has no stretch, and is uncomfortable to wear. Finally, if the fabric is folded back on itself, an electrical short will occur. Thus, special insulative coatings or substrates must be used which further render the fabric uncomfortable to wear.

Others have designed textile fabrics with conductive fibers for electrically interconnecting two electronic components. See U.S. Pat. Nos. 6,080,690 and 5,906,004 incorporated herein by this reference. Again, the main idea is that the whole garment is made of this special fabric. As such, a sensor can be electrically connected to a controller right on the garment. Still, routing of the data or power between the devices is limited without extensive formation of electrical junctions in the fabric—a very cumbersome manufacturing process. In addition, such garments are also uncomfortable and cannot withstand repeated wash cycles. See also U.S. Pat. No. 3,414,666 incorporated herein by this reference.

Commonly owned U.S. Pat. No. 6,727,197, incorporated herein by this reference, discloses designs of textile materials with integrated data or power buses which are simple to manufacture, pleasing in appearance, comfortable, washable, which wear well, which do not add significant weight, which are corrosion resistant, which do not impede mobility, which exhibit high fatigue strengths, and which also properly meet or exceed the electrical interface and shielding requirements of the specific application, be it military or consumer-based.

The present invention more particularly relates to physiological sensing systems as they pertain to wearable electronics. Such systems (e.g., garments) are useful for ambulatory/home monitoring (prophylaxis, diagnosis and/or treatment), in-hospital post-operative monitoring, athletic performance training, infant respiration monitoring for the detection of sudden infant death syndrome, and the like. There has been a lot of activity in this field and in one example it is proposed to include conductive electrocardiogram electrodes and inductive plethysmographic sensors sewn, embroidered, embedded or otherwise attached to a garment such as a shirt with an adhesive. See, for example, U.S. Pat. No. 6,047,203 incorporated herein by this reference.

To date, however, the applicants are unaware of a marketable system which employs low profile sensors held in position against the body throughout a typical range of movements for mechanical and electrical coupling. And, although the prior art teaches garments with integral electrodes and sensors, there is a general failure in the art to consider a non-intrusive, conformable, comfortable integrated data/power bus for providing power to the sensors and electrodes (as required) and for routing sensor/electrode signals to the appropriate processing and/or transmission circuitry.

Any viable system will probably be required to include physiological sensors, electrodes, a textile data/power bus with the appropriate connectors and conductors, sensor conditioning/processing capability, and a power source. Optional elements could be body worn or externally located for analysis and warning features and also include a communication system to support data transmission. A preferred system would include a textile-based elastic body conforming garment including textile fibers formed using knitting, weaving, or braiding techniques and incorporating elastic fiber elements such as Lycra. The sensors would include one or more physiological sensors such as ECG or R-wave sensors, EMG sensors, a respiration sensor, and perhaps skin temperature and body position and motion sensors. Preferably, the sensors would be integral to the garment and operate without the requirement of any user manipulation. Gels and adhesives would preferably not be required. The sensors and their associated electronics should be modular and detachable from the garment for replacement or maintenance. The data/power bus should also be integrated into the garment textile structure to minimize intrusiveness and to maximize user comfort and convenience. The data/power bus should also be transparent to the user and require minimal user manipulation after the system has been donned. The garment should be moisture and temperature resistant for operation under typical environmental conditions, and could include a combination of reusable washable elements and, in some examples, disposable elements. Integral connectors would allow the sensors and electronics to be detached for washing and the remaining garment should survive numerous wash cycles. In another possibility, the sensors and electronics of the system are permanently attached to the garment if it can be manufactured at such a cost that it can be disposed of.

A review of the prior art reveals no system which meets the above criteria for a viable physiological monitoring garment.

SUMMARY OF THE INVENTION

It is therefore an object of this invention to provide an improved physiological monitoring garment.

It is a further object of this invention to provide a more comfortable and more robust physiological monitoring garment.

It is a further object of this invention to provide a physiological monitoring garment that does not impede mobility and is simple to manufacture.

It is a further object of this invention to provide a physiological monitoring garment that is useful for numerous applications such as ambulatory home and outpatient monitoring and athletic performance training.

It is a further object of this invention to provide a physiological monitoring garment including an integrated stretchable power/data bus for use with a variety of sensors.

It is a further object of this invention to provide an improved flexible low profile sensor, as well as to provide an improved respiration monitoring device, each of which may be used in conjunction with the improved physiological monitoring garment.

The invention results from the realization that an improved physiological monitoring garment can be achieved with an elongate stretchable textile data/power bus disposed in an elastic fabric having one or more sensors connected to it. The invention results from the further realization that an improved sensor useful with the physiological monitoring garment can be achieved with a flexible circuit board configured as an electrode with a conductive portion on one surface and a dielectric material on the conductive portion. The flexibility helps prevent bridging and capacitive coupling avoids the necessity of conductive gels or adhesives. The invention also results from the further realization that an improved respiration monitoring device useful with the physiological monitoring garment can be achieved with an elongate stretchable textile member and conductive components associated therewith, where the textile member provides dielectric separation between the conductive components such that expansion and contraction of the textile member results in a change in the spacing between the conductive components, resulting in a change of capacitance, by which respiration can be measured.

The subject invention, however, in other embodiments, need not achieve all these objectives and the claims hereof should not be limited to structures or methods capable of achieving these objectives.

This invention features a physiological monitoring garment including a first elastic fabric portion, a second elastic fabric portion, and an elongate stretchable textile data/power bus between the first fabric portion and the second fabric portion. The elongate stretchable textile data/power bus includes a plurality of integral conductors, woven, knitted, or braided along the length thereof. One or more sensors are connected to the elongate stretchable textile data/power bus. The first fabric portion may be the upper portion of a shirt and the second fabric portion may be the lower portion of the shirt. The first fabric portion may be connected to the second fabric portion via the elongate stretchable textile data/power bus. The elongate stretchable textile data/power bus may be attached to the garment between the first fabric portion and the second fabric portion. The physiological monitoring garment may further include at least a third elastic fabric portion and at least a second elongate stretchable textile data/power bus including a plurality of integral conductors, woven, knitted, or braided along the length thereof, and one or more sensors connected to the at least second elongate stretchable textile data/power bus. The plurality of conductors may be woven, knitted, or braided in a strain relief pattern. The plurality of conductors may include conductors for data transfer, conductors for power transfer, and conductors structured and arranged to form an electronic shield for reducing noise. Also, a coating of conductive material may be disposed on the elongate stretchable textile data/power bus to form an electrical shield for reducing noise. The strain relief pattern may be out of the plane of the elongate stretchable textile data/power bus or in the plane of the elongate stretchable textile data/power bus. Connectors may connect the one or more sensors to the elongate stretchable textile data/power bus, and the connectors may be insulation displacement connectors.

A sensor connected to the elongate stretchable textile data/power bus may include a respiration monitoring device, and the respiration monitoring device may include at least a first elongate stretchable textile member, a first conductive component associated with said textile member, and a second conductive component associated with said textile member. Threads of the textile member provide dielectric separation between the at least first and second conductive components so that the expansion and contraction of the textile member results in a change in the spacing between the first and second conductive components for measuring change in capacitance. The first conductive component may include woven, knitted, or braided conductive threads integral with the first textile member. There may be a plurality of elongate stretchable textile members adjacent each other, and each may include integral woven, knitted, or braided conductive threads. The respiration monitoring device may be disposed in or on the garment proximate the data/power bus.

Another sensor connected to the elongate stretchable textile data/power bus may include a flexible circuit board configured as an electrode, a conductive portion on one surface of the flexible circuit board, and a dielectric material on the conductive portion. An opposing surface of the flexible circuit board may include signal conditioning circuitry, or the flexible circuit board may be connected to a second flexible circuit board that includes signal conditioning circuitry. Conductive traces may interconnect the conductive portion with the signal conditioning circuitry. The conductive portion may be a conductive foil laminated on the flexible circuit board. The conductive portion may be conductive material sputtered or plated on the flexible circuit board. The dielectric material may be material sputtered, laminated, evaporated, or spun onto the conductive portion. The sensor may include an insulating edge for preventing short circuits. The sensor may be configured to include at least two electrodes, and each of the electrodes may each include signal conditioning circuitry.

This invention also features a physiological monitoring garment including an elastic fabric portion, at least one elongate stretchable textile data/power bus disposed on the elastic fabric portion, the elongate stretchable textile data/power bus including a plurality of integral conductors, woven, knitted, or braided along the length thereof, and one or more sensors connected to the elongate stretchable textile data/power bus. The plurality of conductors may be woven, knitted, or braided in a strain relief pattern. The plurality of conductors may include conductors for data transfer, conductors for power transfer, and conductors structured and arranged to form an electronic shield for reducing noise. A coating of conductive material may be disposed on the elongate stretchable textile data/power bus to form an electrical shield for reducing noise. The strain relief pattern may be out of the plane of the elongate stretchable textile data/power bus or in the plane of the elongate stretchable textile data/power bus. Connectors may connect the one or more sensors to the elongate stretchable textile data/power bus, and the connectors may be insulation displacement connectors.

A sensor connected to the elongate stretchable textile data/power bus may include a respiration monitoring device, and the respiration monitoring device may include at least a first elongate stretchable textile member, a first conductive component associated with said textile member, and a second conductive component associated with said textile member. Threads of the textile member provide dielectric separation between the at least first and second conductive components so that the expansion and contraction of the textile member results in a change in the spacing between the first and second conductive components for measuring change in capacitance. The first conductive component may include woven, knitted, or braided conductive threads integral with the first textile member. There may be a plurality of elongate stretchable textile members adjacent each other, and each may include integral woven, knitted, or braided conductive threads. The respiration monitoring device may be disposed in or on the garment proximate the data/power bus.

Another sensor connected to the elongate stretchable textile data/power bus may include a flexible circuit board configured as an electrode, a conductive portion on one surface of the flexible circuit board, and a dielectric material on the conductive portion. An opposing surface of the flexible circuit board may include signal conditioning circuitry, or the flexible circuit board may be connected to a second flexible circuit board that includes signal conditioning circuitry. Conductive traces may interconnect the conductive portion with the signal conditioning circuitry. The conductive portion may be a conductive foil laminated on the flexible circuit board. The conductive portion may be conductive material sputtered or plated on the flexible circuit board. The dielectric material may be material sputtered, laminated, evaporated, or spun onto the conductive portion. The sensor may include an insulating edge for preventing short circuits. The sensor may be configured to include at least two electrodes, and each of the electrodes may each include signal conditioning circuitry.

This invention further features a physiological monitoring garment including an elongate stretchable textile data/power bus including a plurality of integral conductors, woven, knitted, or braided along the length thereof, and one or more sensors connected to the elongate stretchable textile data/power bus.

This invention also features a physiological monitoring garment including a first fabric portion, a second fabric portion, and an elongate stretchable textile data/power bus between the first fabric portion and the second fabric portion. The elongate stretchable textile data/power bus includes a plurality of integral conductors, woven, knitted, or braided along the length thereof in a strain relief pattern. A respiration monitoring device is connected to the textile data/power bus and includes a first elongate stretchable textile member, a first conductive component associated with the textile member, and a second conductive component associated with the textile member. Threads of the textile member provide dielectric separation between the first and second conductive components so that the expansion and contraction of said textile member results in a change in the spacing between the first and second conductive components. At least two sensors may be connected to the textile data/power bus. The sensors each may include a flexible circuit board configured as an electrode, a conductive portion on one surface of the flexible circuit board, and a dielectric material on the conductive portion.

This invention also features a physiological monitoring garment including an elastic fabric portion, at least one elongate stretchable textile data/power bus disposed on the elastic fabric portion, the elongate stretchable textile data/power bus including a plurality of integral conductors, woven, knitted, or braided along the length thereof in a strain relief pattern, and a respiration monitoring device connected to the textile/data power bus. The respiration monitoring device includes a first elongate stretchable textile member, a first conductive component associated with the textile member, a second conductive component associated with the textile member, and threads of the textile member providing dielectric separation between the first and second conductive components so that the expansion and contraction of the textile members results in a change in the spacing between the first and second conductive components. The physiological monitoring garment also includes at least two sensors connected to the textile data/power bus, the sensors each including a flexible circuit board configured as an electrode, a conductive portion on one surface of the flexible circuit board, and a dielectric material on the conductive portion.

This invention further features a physiological monitoring garment including a first fabric portion, a second fabric portion, and an elongate stretchable textile data/power bus between the first fabric portion and the second fabric portion, the elongate stretchable textile data/power bus including a plurality of integral conductors, woven, knitted, or braided along the length thereof in a strain relief pattern. The physiological monitoring garment may include at least a third elastic fabric portion and at least a second elongate stretchable textile data/power bus including a plurality of integral conductors, woven, knitted, or braided along the length thereof, and one or more sensors connected to the at least second elongate stretchable textile data/power bus.

This invention also features a physiological monitoring garment including an elastic fabric portion and at least one elongate stretchable textile data/power bus disposed on the elastic fabric portion, the elongate stretchable textile data/power bus including a plurality of integral conductors, woven, knitted, or braided along the length thereof in a strain relief pattern.

This invention also features a physiological monitoring garment including a first fabric portion, a second fabric portion, and an elongate stretchable textile data/power bus between the first fabric portion and the second fabric portion. The elongate stretchable textile data/power bus includes a plurality of integral conductors, woven, knitted, or braided along the length thereof in a strain relief pattern. A respiration monitoring device is connected to the data/power bus and includes a first elongate stretchable textile member, a first conductive component associated with the textile member, a second conductive component associated with the textile member, and threads of the textile member providing dielectric separation between the first and second conductive components so that the expansion and contraction of the textile member results in a change in the spacing between the first and second conductive components. The physiological monitoring garment may include at least a third elastic fabric portion and at least a second elongate stretchable textile data/power bus including a plurality of integral conductors, woven, knitted, or braided along the length thereof, and one or more sensors connected to the at least second elongate stretchable textile data/power bus.

This invention further features a physiological monitoring garment including an elastic fabric portion, at least one elongate stretchable textile data/power bus disposed on the elastic fabric portion, the elongate stretchable textile data/power bus including a plurality of integral conductors, woven, knitted, or braided along the length thereof in a strain relief pattern, and a respiration monitoring device connected to the data/power bus. The respiration monitoring device includes a first elongate stretchable textile member, a first conductive component associated with the textile member, a second conductive component associated with the textile member, and threads of textile member providing dielectric separation between the first and second conductive components so that the expansion and contraction of the textile member results in a change in the spacing between the first and second conductive components.

This invention further features a physiological monitoring garment including a first fabric portion, a second fabric portion, an elongate stretchable textile data/power bus between the first fabric portion and the second fabric portion, the elongate stretchable textile data/power bus including a plurality of integral conductors, woven, knitted, or braided along the length thereof in a strain relief pattern, and at least one sensor connected to the textile data/power bus, the sensor including a flexible circuit board configured as an electrode, a conductive portion on one surface of the flexible circuit board, and a dielectric material on the conductive portion. The physiological monitoring garment may include at least a third elastic fabric portion and at least a second elongate stretchable textile data/power bus including a plurality of integral conductors, woven, knitted, or braided along the length thereof, and one or more sensors connected to the at least second elongate stretchable textile data/power bus.

This invention also features a physiological monitoring garment including an elastic fabric portion, at least one elongate stretchable textile data/power bus disposed on the elastic fabric portion, the elongate stretchable textile data/power bus including a plurality of integral conductors, woven, knitted, or braided along the length thereof in a strain relief pattern. At least one sensor is connected to the textile data/power bus, the sensor including a flexible circuit board configured as an electrode, a conductive portion on one surface of the flexible circuit board, and a dielectric material on the conductive portion.

This invention also features a data/power bus for a garment, the data/power bus including an elongate stretchable textile member and a plurality of conductors woven, knitted, or braided along the length thereof integral with threads of the elongate stretchable textile member in a strain relief pattern. The strain relief pattern may be out of the plane of the elongate stretchable data/power bus or the strain relief pattern may be in the plane of the elongate stretchable data/power bus. The data/power bus may include connectors for attaching sensors to the data/power bus. The plurality of conductors may include conductors for data transfer, conductors for power transfer, and conductors structured and arranged to form an electronic shield for reducing noise.

This invention further features a respiration monitoring device including a first elongate stretchable textile member, a first conductive component associated with the textile member, a second conductive component associated with the textile member, and threads of the textile member providing dielectric separation between the first and second conductive components so that the expansion and contraction of the textile member results in a change in the spacing between the first and second conductive components. The first conductive component may include woven, knitted, or braided conductive threads integral with the textile member. There may be first and second elongate stretchable textile members adjacent each other and each may include integral woven, knitted, or braided conductive threads.

This invention also features a sensor for a garment including a flexible circuit board configured as an electrode, a conductive portion on one surface of the flexible circuit board, and a dielectric material on the conductive portion. The opposing surface of the flexible circuit board may include signal conditioning circuitry. The flexible circuit board may be connected to a second flexible circuit board including signal conditioning circuitry. Conductive traces may interconnect the conductive portion with the signal conditioning circuitry. The conductive portion may be a conductive foil laminated on the flexible circuit board or the conductive portion may be conductive material sputtered or plated on the flexible circuit board. The dielectric material may be material sputtered, laminated, evaporated, or spun onto the conductive portion.

BRIEF DESCRIPTION OF THE DRAWINGS

Other objects, features and advantages will occur to those skilled in the art from the following description of a preferred embodiment and the accompanying drawings, in which:

FIG. 4 is an enlarged schematic partial view of another form of the elongate stretchable textile data/power bus of the physiological monitoring garment of FIG. 1A;

FIG. 5 is a schematic view of the elongate stretchable textile data/power bus of FIG. 4;

FIG. 12 is a schematic view of the major components of one prior art ECG sensor;

DISCLOSURE OF THE PREFERRED EMBODIMENT

Figure 1A:
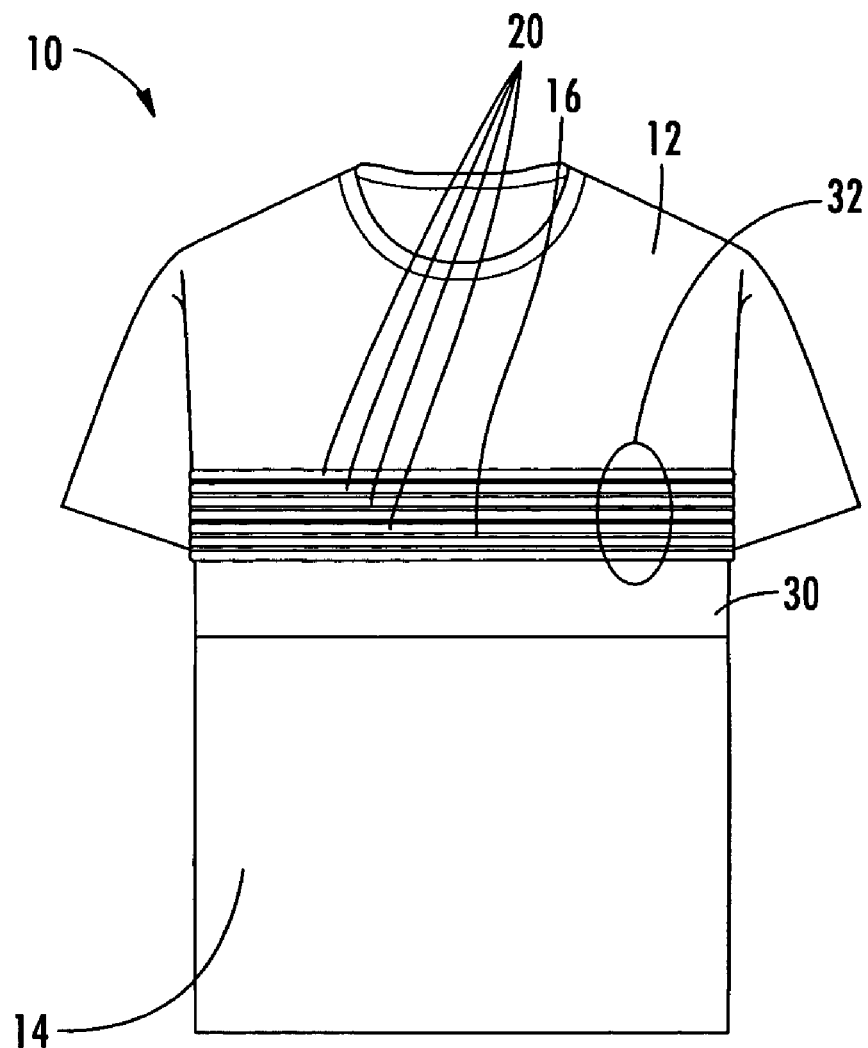
FIG. 1A is a schematic view of one example of a physiological monitoring garment in accordance with the present invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

One embodiment of a physiological monitoring garment in accordance with the present invention is shown at 10 in FIG. 1A. As shown, physiological monitoring garment 10 includes elastic fabric portions 12 and 14. Elongate stretchable textile data/power bus 16 is disposed between elastic fabric portions 12 and 14. Elongate stretchable textile data/power bus 16 includes a plurality of integral conductors 20 woven, knitted, or braided along the length of elongate stretchable textile data/power bus 16 and one or more sensors 30, 32 connected to the elongate stretchable textile data/power bus. These latter features are discussed more fully below, as well as the multiple sensors which are not limited to any particular type or number and which may be attached to elongate stretchable textile data/power bus 16. In the example shown, the elastic fabric portion 12 is connected to the elastic fabric portion 14 via elongate stretchable textile data/power bus 16. Elongate stretchable textile data/power bus 16 is attached to garment 10 between elastic fabric portion 12 and elastic fabric portion 14. As shown, elastic fabric portion 12 is the upper portion of a shirt, and fabric portion 14 is the lower portion of a shirt, although this is not a necessary limitation of the invention. Elongate stretchable textile data/power bus 16 may also be located at any point between elastic fabric portions 12 and 14. Further, elongate stretchable textile data/power bus 16 or another similar bus may be located between the right and left elastic fabric portions of the garment such that it extends vertically through physiological monitoring garment 10 rather than around the torso of the wearer.

Figure 1B:
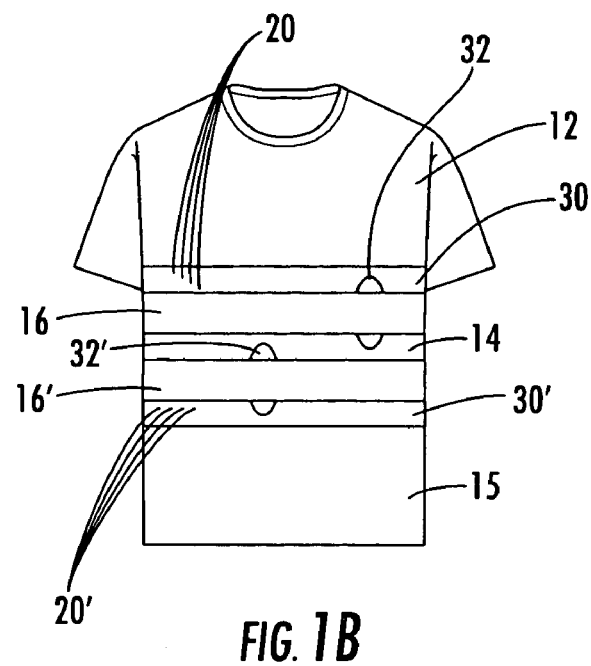
FIG. 1B is a schematic view of another example of a physiological monitoring garment in accordance with the present invention.
Figure 1C:
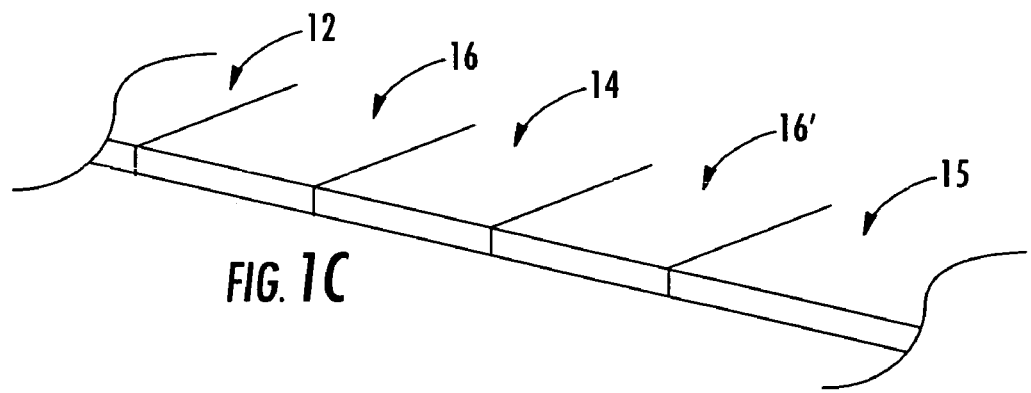
FIG. 1C is an enlarged schematic cross-sectional view of the physiological monitoring garment of FIG. 1B.

Also, physiological monitoring garment 10, FIG. 1B, may include two or more elongate stretchable textile data/power buses 16 and 16' as desired for a particular application. In such an example, elongate stretchable textile data/power bus 16 is between fabric portions 12 and 14 and elongate stretchable textile data/power bus 16' is between fabric portions 14 and 15. Elongate stretchable textile data/power bus 16, FIG. 1C, may connect fabric portions 12 and 14, and elongate stretchable textile data/power bus 16' may connect fabric portions 14 and 15. Elongate stretchable textile data/power bus 16' may also include a plurality of conductors 20' (not shown), woven, knitted, or braided along the length of elongate stretchable textile data/power bus 16'. Elongate stretchable textile data/power bus 16' may also include one or more sensors 30', 32' attached to it. Also, elongate stretchable textile data/power bus 16, FIG. 1D, may be disposed on fabric portion 12 of physiological monitoring garment 10, for example, as shown in FIG. 1E in cross-section but not to scale. In the latter case, there is a single fabric portion 12 instead of multiple fabric portions. Fabric portion 12 may be in the form of a sports bra or tube top, for example. Elongate stretchable textile data/power bus 16 may be attached to fabric portion 12 by any known appropriate means. Overall, there may be any number of fabric portions as desired, and there may be any number of desired elongate stretchable textile data power buses, also as desired or needed for a particular application.

Figure 1D:
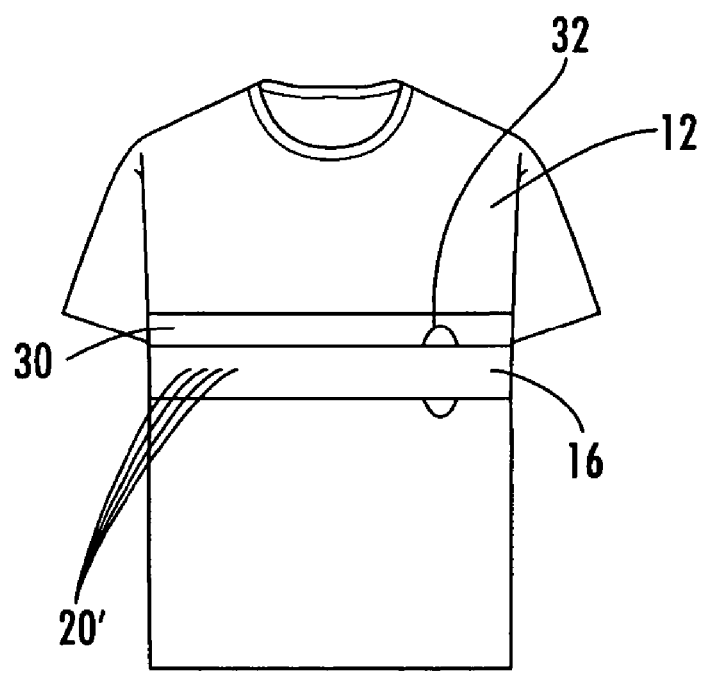
FIG. 1D is another form of the physiological monitoring garment in accordance with the present invention with a single fabric section.
Figure 1E:
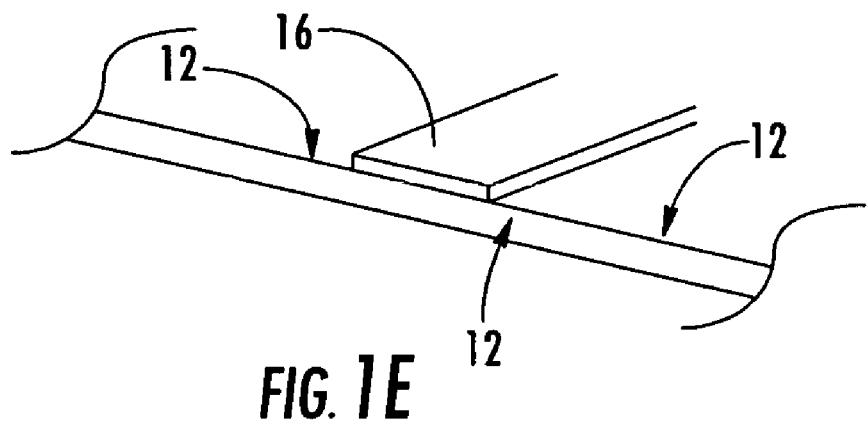
FIG. 1E is an enlarged schematic cross-sectional view of the physiological monitoring garment of FIG. 1D.

In another example, physiological monitoring garment 10 including elongate stretchable textile data/power bus 16 as shown in FIG. 1D, may be worn as a strap directly on the subject or patient underneath the fabric portion (not shown), without being attached to a fabric portion, such as fabric portion 12, at all.

In all embodiments, the elastic fabric portions, including elastic fabric portions 12, 14 and 15, FIGS. 1A-1E, preferably include an elastic material such as Lycra, which has radial and longitudinal stretchability. The elastic material, i.e. Lycra, is incorporated with textile fibers such as nylon, polyester, silk, or cotton, by weaving, knitting or braiding. This allows physiological monitoring garment 10 to be form fitting yet comfortable, such that various sensors as described below are properly held in position. Furthermore, the moisture sensitivity of physiological monitoring garment 10 may be reduced using water-repellant coatings, and biocidal materials may be incorporated into physiological monitoring garment 10 to minimize bacterial growth. In any of the foregoing examples, the elongate stretchable textile data/power bus of the physiological monitoring garment may include integral conductors, connectors, materials and/or sensors as will now be more fully described.

Figure 2:
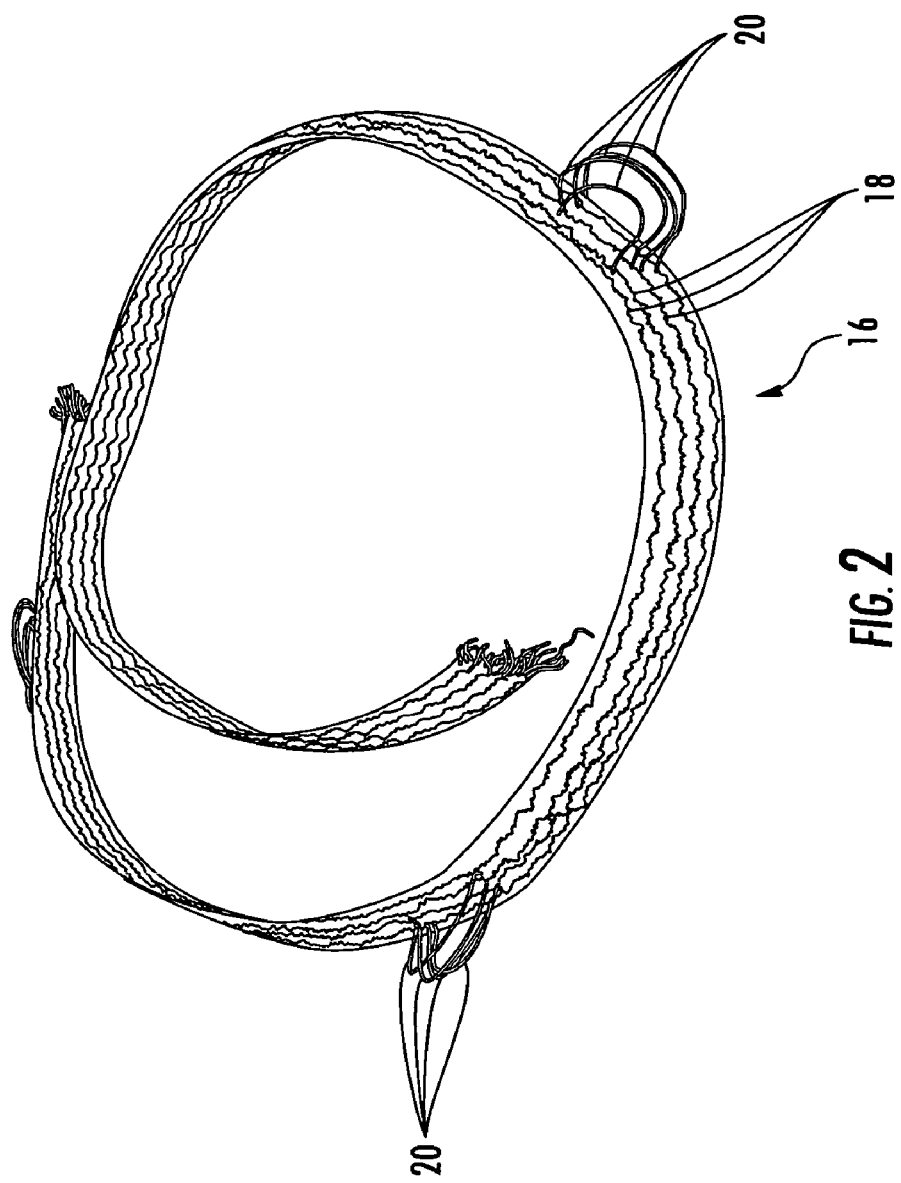
FIG. 2 is a schematic view of one form of the elongate stretchable textile data/power bus of the physiological monitoring garment of FIG. 1A.

As noted above, elongate stretchable textile data/power bus 16, FIG. 2, typically includes a plurality of integral conductors 20 which are woven, knitted, or braided along the length of stretchable textile data/power bus 16. In FIG. 2 integral conductors 20 are shown as woven with external loops from elongate stretchable textile data/power bus 16. This can also be effective for making electrical connections, as discussed further below. In use, integral conductors 20 may not be visible to the user. Stretchable textile data/power bus 16 also includes textile portion 18. Textile portion 18 of physiological monitoring garment 10 may be comprised of either natural or synthetic textile materials such as polyester, cotton or nylon. In a preferred embodiment, textile portion 18 is comprised of Lycra combined with natural or synthetic textile materials through weaving, knitting, or braiding, in order to provide elasticity.

Figure 3A:
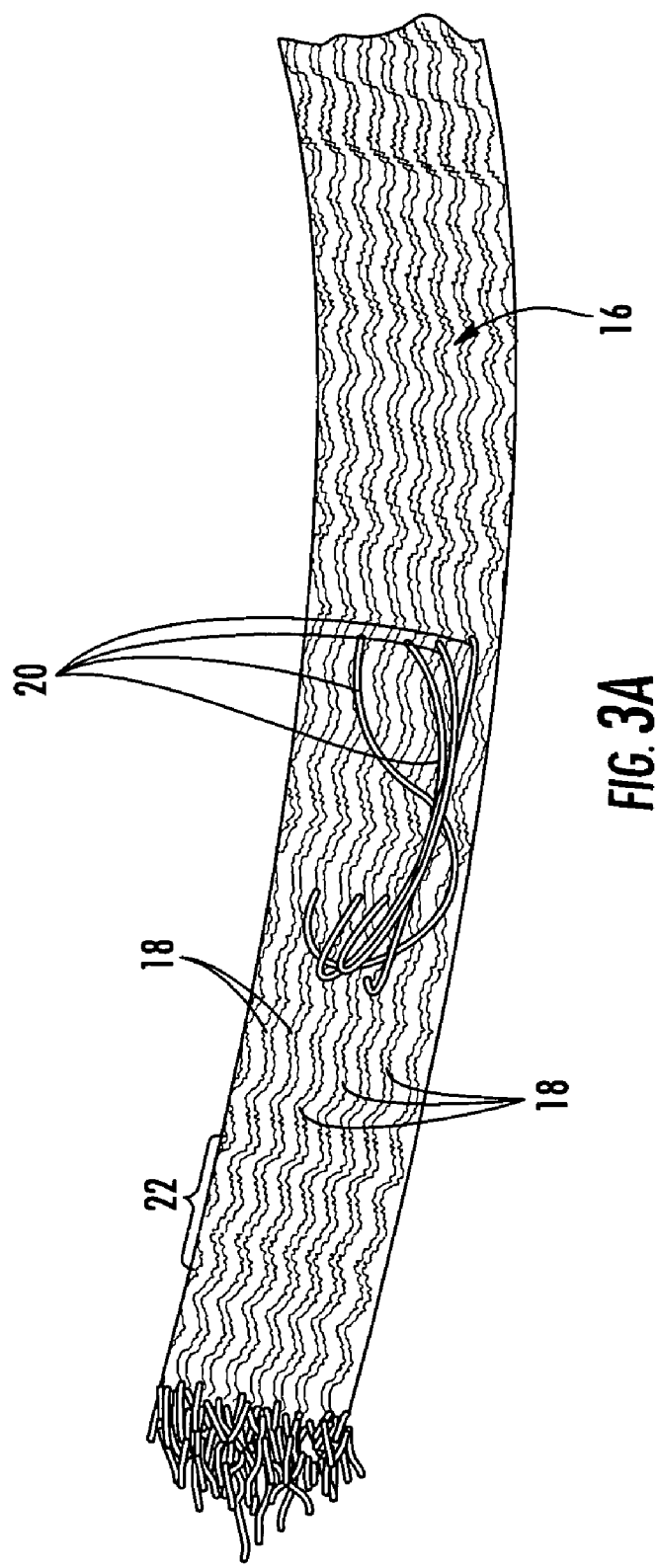
FIG. 3A is an enlarged schematic partial view of the elongate stretchable textile data/power bus of FIG. 2 showing breakouts in the fabric where individual conductive components may be accessed for connection.
Figure 3B:
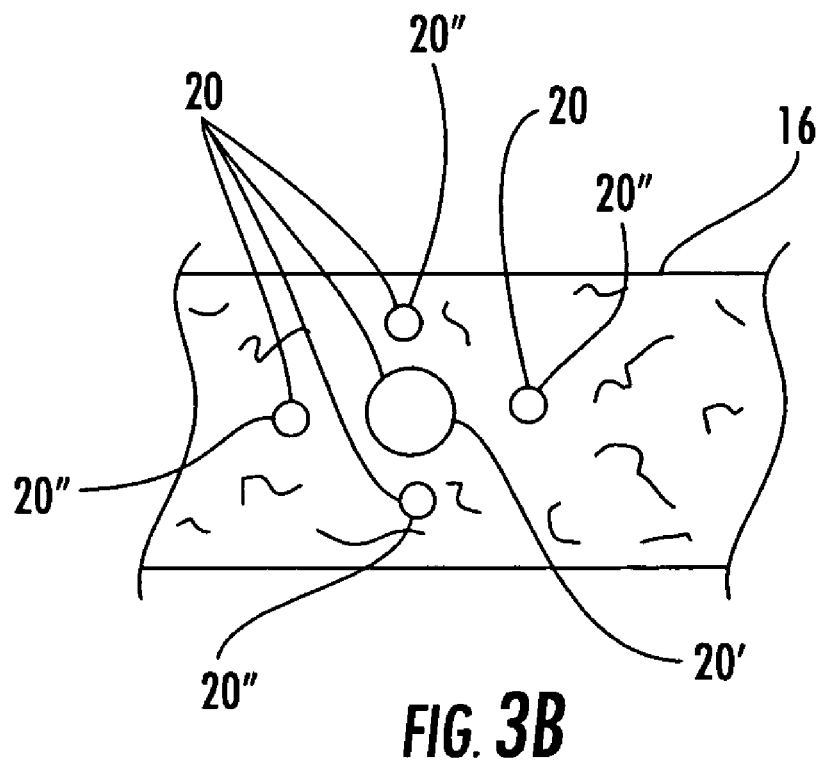
FIG. 3B is an enlarged cross-sectional view of a portion of the elongate stretchable textile data/power bus of FIG. 3A.
Figure 3C:
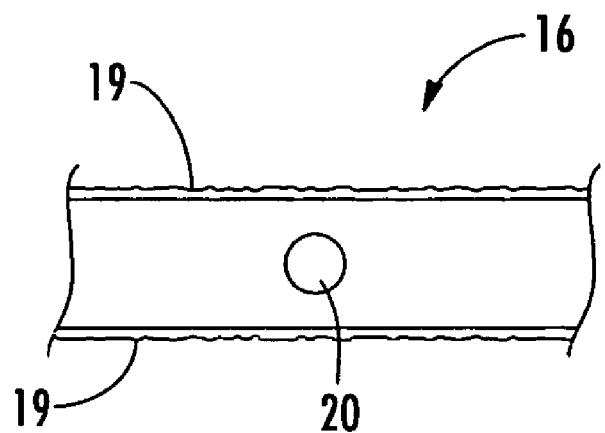
FIG. 3C is an enlarged cross-sectional side view of a portion of the elongate stretchable textile data/power bus of FIG. 3A.

Typically, plurality of integral conductors 20 in stretchable textile data/power bus 16 are woven, knitted, or braided in a strain relief pattern as described below. When the subject invention is in use, textile portion 18 expands or stretches, and the strain relief pattern of integral conductors 20 allows them to lengthen and shorten. FIG. 3A is an enlarged view of elongate stretchable textile data/power bus 16 with plurality of integral conductors 20 woven in strain relief pattern 22 in the plane of elongate stretchable textile data/power bus 16. Integral conductors 20, FIG. 3B, include conductors 20' for data transfer and power transfer. Integral conductors 20 may also include conductors 20" structured and arranged to form an electrical shield for reducing noise, as known in the art. Alternatively, a coating of conductive material 19, FIG. 3C, such as metal, may be disposed on elongate stretchable textile data/power bus 16 to form an electrical shield to reduce noise.

In another embodiment, the strain relief pattern 25, FIG. 4, for conductors 20, shown as 20a . . . 20n, is perpendicular to or out of the plane of elongate stretchable textile data/power bus 16. In this embodiment, integral conductors 20a . . . 20n may be partially visible to the user. Alternatively, the strain relief pattern may be a combination of in plane and out of plane (not shown). Either in plane strain relief pattern 22 or out of plane strain relief pattern 25 of integral conductors 20 and 20a . . . 20n may resemble a sinusoidal pattern.

In one example, strain relief patterns 22 and 25, FIGS. 3A and 4, are achieved by weaving, knitting or braiding integral conductors 20 and 20a . . . 20n when textile portion 18 is fully or partially stretched. Integral conductors 20, 20a . . . 20n may include conventional insulated cables or wires. Thus, when textile portion 18 is released from its stretched configuration, integral conductors 20 form a strain relief pattern whereby slack is introduced into integral conductors 20. In this way, when textile portion 18 of stretchable textile data/power bus 16 is expanded or stretched during use, damage to integral conductors 20 due to stretching forces is lessened or eliminated.

Figure 6:
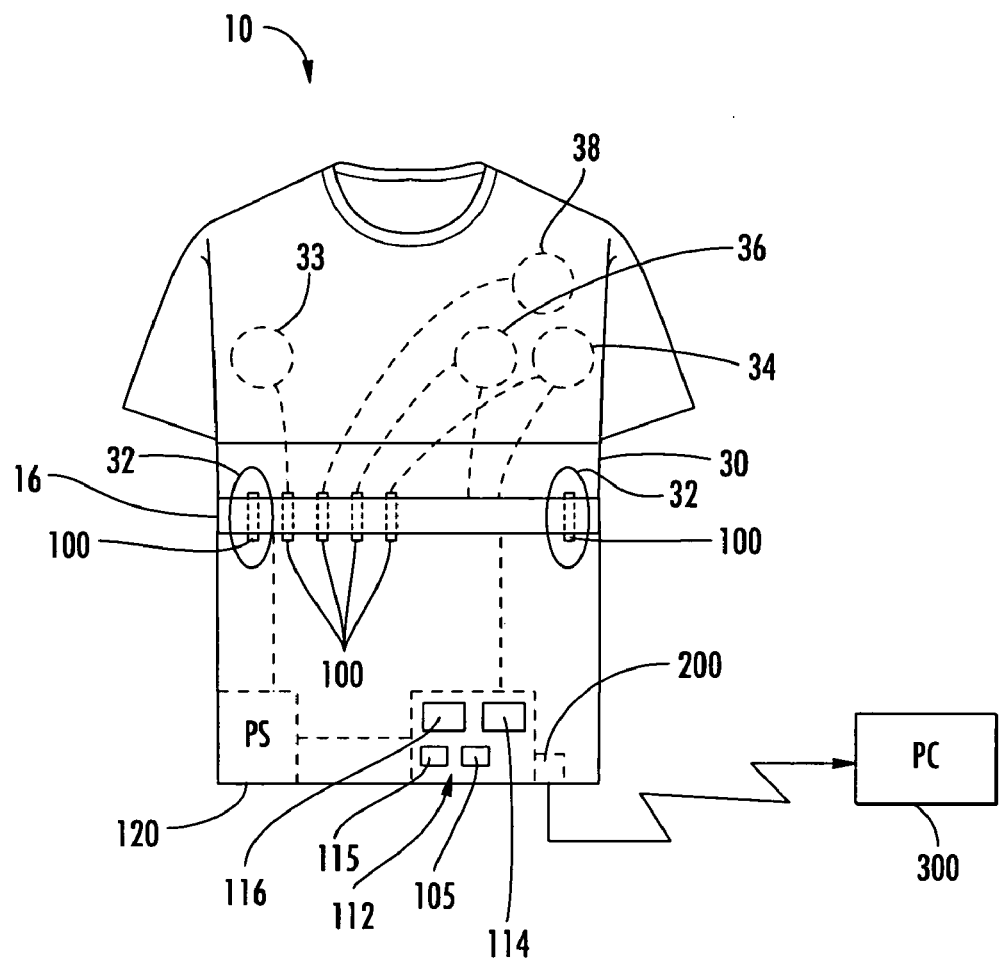
FIG. 6 is a schematic view of the physiological monitoring garment of FIG. 1A including sensors connected thereto.

Sensors 30-38, FIG. 6 may be mechanically attached to physiological monitoring garment 10 through energy welding processes including ultrasonic welding, thermal melding, RF welding, or other suitable techniques. Preferably, however, sensors 30-38 are configured to take greater advantage of physiological monitoring garment 10 by being attachable to and detachable from stretchable textile data/power bus 16 via sensor connectors 100. Elongate stretchable textile data/power bus 16 may include one or more connectors 100 for connecting sensors 30-38, which are included in physiological monitoring garment 10, to elongate stretchable textile data/power bus 16. Insulation displacement (IDC) type connectors, which are generally available off the shelf, or end type connectors, may be used as connectors 100 to attach sensors 30-38 to integral conductors 20. Such IDC connectors are best shown in FIG. 5 at 100. Alternatively, integral conductors 20, FIG. 3A, may be spliced or broken to allow for connections to sensors 30-38, FIG. 6. It will be apparent that, as necessary or desired, sensors 30-38 may be attached to one another, and then connected to elongate stretchable textile data/power bus 16.

The outputs of sensors 30-38, FIG. 6, are typically fed into conditioning electronics 105 in processing hub 112, which includes microprocessor 115, and may include an analog-to-digital converter 114 and filters 116. Microprocessor 115 will also typically include appropriate software/algorithms for determining the applicable health status of the patient from the data and information received. Processing hub 112 and power supply 120 are electrically connected to elongate stretchable textile data/power bus 16. Preferably, processing hub 112 and power supply 120 are incorporated into physiological monitoring garment 10, but this is not a necessary limitation of the invention. For example, processing hub 112 and power supply 120 may attach to or snap onto the patient's belt or be hip mounted, or otherwise be carried by the patient, depending on the needs of a particular desired application. Additionally, power source 120 is preferably not separate from processing hub 112 but is in one package (not shown) as part of a hip mounted package, for example.

Additionally, a wireless telemetry system 200 may be connected to elongate stretchable textile data/power bus 16 of physiological monitoring garment 10 for wireless communication via radio frequency or other conventional means. Wireless telemetry system 200 may also be incorporated into physiological monitoring garment 10 or part of a hip mounted package with processing hub 112 and/or power supply 120, for remote connection between the patient user and personal computer 300 at a distance.

Thus, physiological monitoring garment 10 including elongate stretchable textile data/power bus 16 provides the capability of data and power routing from a multiplicity of sensors 30-38, to and from processing hub 112 and power supply 120, and does so while effectively and comfortably maintaining pressure on sensors 30-38 to hold sensors 30-38 in place against the patient or subject. Physiological monitoring garment 10 further allows sensors 30-38 to be detachable via connectors 100 in stretchable textile data/power bus 16. This gives physiological monitoring garment 10 adaptability and washability without risk of damage to potentially fragile and/or expensive sensors.

The physiological monitoring garment of the present invention is not limited to any particular type of sensor, however. Any number or type of sensors may be utilized, depending on a particular desired application or health status information desired. Sensors which may be connected to elongate stretchable textile/data power bus 16 in physiological monitoring garment 10 include electrocardiogram (ECG) sensors 32, sensors for muscle activity (EMG) 33, skin temperature 34, body orientation 36, and motion sensors 38, and may include associated alarm systems to alert the patient to various physiological conditions.

Another type of sensor for use with physiological monitoring garment 10 is respiration sensor 30. Preferably, respiration sensor 30 is an improved respiration sensor for use with physiological monitoring garment 10, namely respiration monitoring device 40, FIGS. 7A-7C. Conventional respiration sensors include impedance pneumography, inductive plethysmography, or measurements of changes in strain (resistive strain gage or piezoelectric), tension or pressure which can be used to infer respiration.

In contrast, respiration monitoring device 40 in accordance with this invention provides textile based capacitive transduction as a means for sensing respiration. Conductive portions act as electrodes and non-conductive textile material acts as a dielectric material between the conductive portions. Particularly, respiration monitoring device 40 includes elongate stretchable textile member 42, and conductive components or members 44 and 46 associated with textile member 42. Textile member 42, including threads 48 of textile member 42, provide dielectric separation between conductive components 44 and conductive component 46 such that expansion and contraction of textile member 42 results in a change in the spacing between conductive components 44 and 46. Conductive components 44 and 46 act as electrodes, and are used to sense the capacitance of textile member 42, which acts as a non-conductive dielectric. Textile member 42 may be comprised of either synthetic or natural textile materials such as polyester, cotton, or nylon.

Figure 7A:
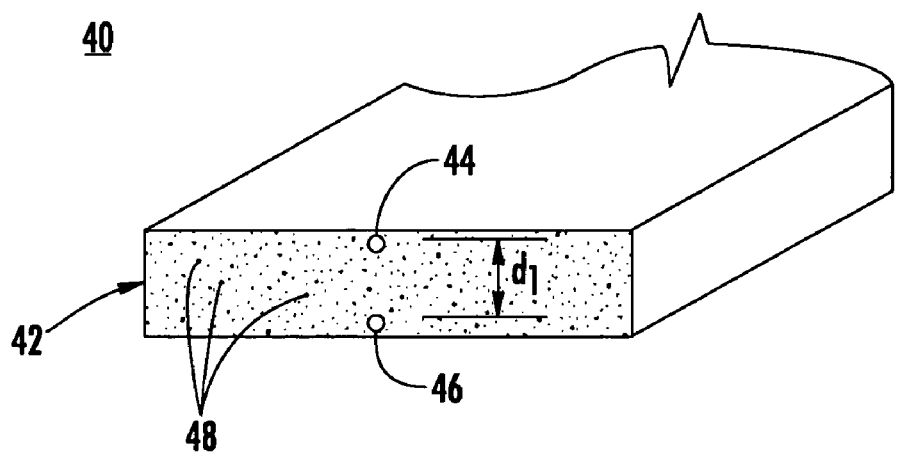
FIGS. 7A-7B are enlarged cross-sectional views of one example of an improved respiration monitoring device in accordance with the present invention.
Figure 7B:
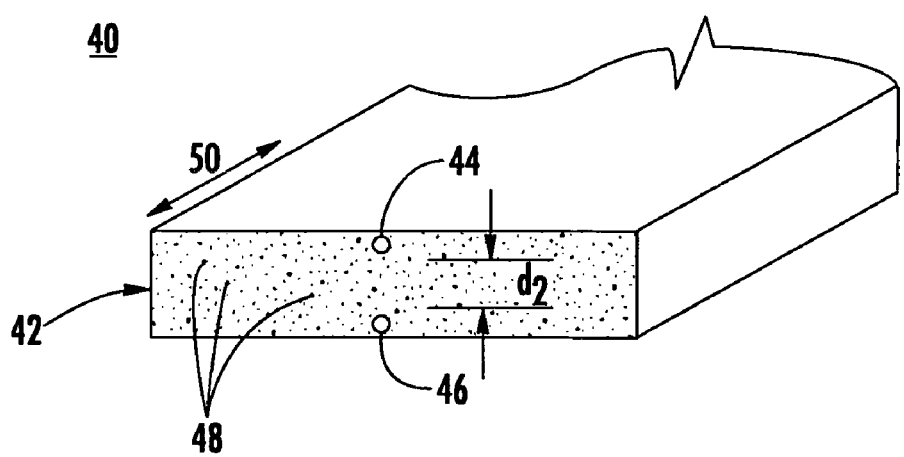
Figure 8:
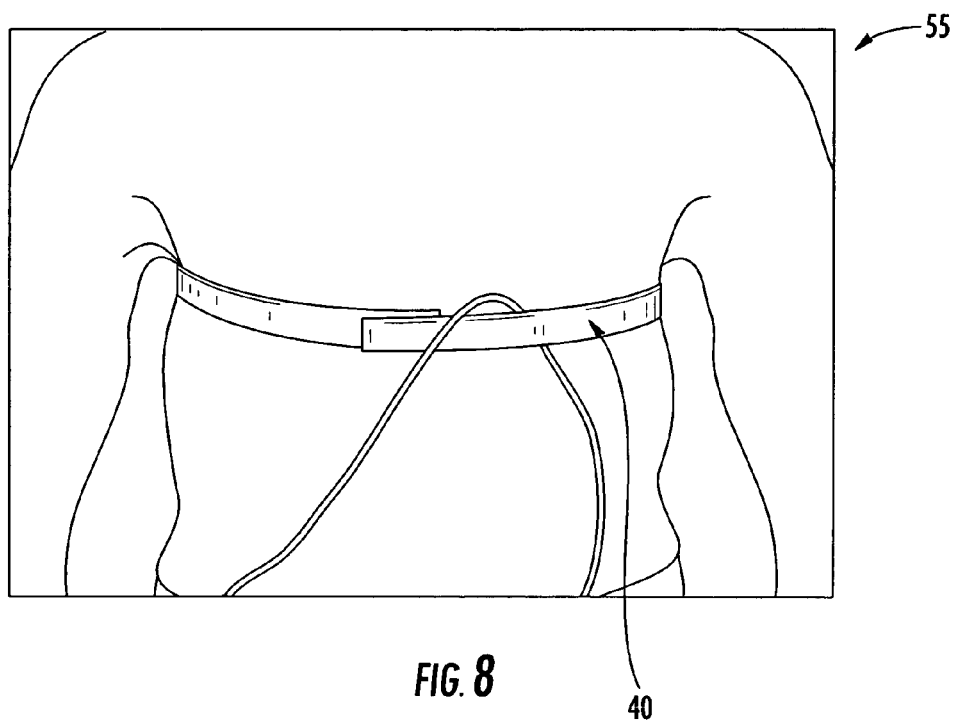
FIG. 8 is a schematic view showing the placement of the improved respiration monitoring device of the subject invention when in use on a subject or patient.

Respiration monitoring device 40 in use on a patient or subject is preferably placed around the patient near the diaphragm of patient 55, FIG. 8. As the patient inhales and exhales, textile member 42, FIGS. 7A and 7B, expands and contracts, thus causing the length of textile member 42 to change. This change in length in turn changes the spacing between conductive components 44 and 46, which changes the capacitance. In general, the theoretical capacitance of a dielectric between two conductive plates is:

$$C=A\epsilon_o/[d+t(1/\epsilon_r-1)] \quad (1)$$

where A is the area of the conductive plates, $\epsilon_o$ is the dielectric of any air between the plates, d is the spacing between the plates, t is the thickness of the dielectric, and $\epsilon_r$ is the dielectric of the material. Therefore, it can be seen that the capacitance of a dielectric material is proportional to the dielectric constant of the material and the thickness of the material or spacing between the electrodes. For respiration monitoring device 40, as textile member 42 is stretched, the spacing between conductive components or members 44 and 46 decreases, decreasing the space between conductive components "electrodes" 44 and 46. Tests have revealed that measured capacitance varies nearly linearly with elongation of respiration monitoring device 40. From this capacitive transduction mechanism, including sensing the change in capacitance, both the type and rate of respiration can be determined.

In further detail, respiration monitoring device 40, FIGS. 7A and 7B, includes textile member 42 having threads 48, as well as conductive components 44 and 46 shown a distance $d_1$ apart. When the subject or patient inhales, for example, textile member 42 stretches lengthwise, as shown at 50, FIG. 7B, along the length of respiration monitoring device 40. As textile member 42 stretches, the distance between conductive components 44 and 46 decreases to a distance $d_2$, where $d_2$ is less than $d_1$. As noted, the change in the spacing between conductive components 44 and 46 changes the capacitance, which is an indication of respiration. Conductive components 44 and 46 may be woven, knitted or braided integral with textile member 42.

Figure 7C:
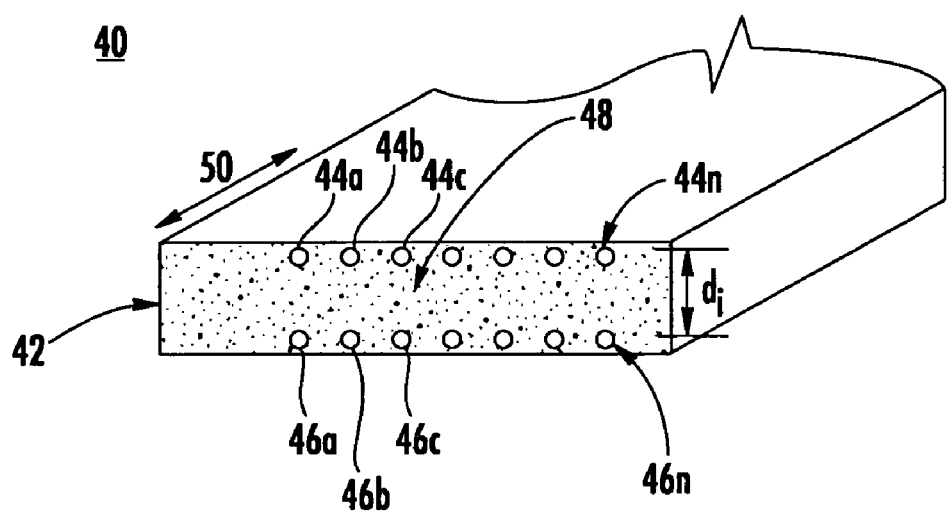
FIG. 7C is an enlarged cross-sectional view of another example of an improved respiration monitoring device in accordance with the present invention.

Also, in another example, there may be a plurality of conductive components 44a ... 44n and 46a ... 46n, FIG. 7C, which may also be woven, knitted or braided integral with textile member 42. The operation of these conductive components will be the same as described above in FIGS. 7A and 7B, that is, as textile member 42 stretches lengthwise, distance $d_1'$ between conductive threads 44a and 46a will decrease. The same will hold true with conductive threads 44b ... 44n and 46b ... 44n. As shown in FIGS. 7A-7C, the stretching is in plane.

Figure 9:
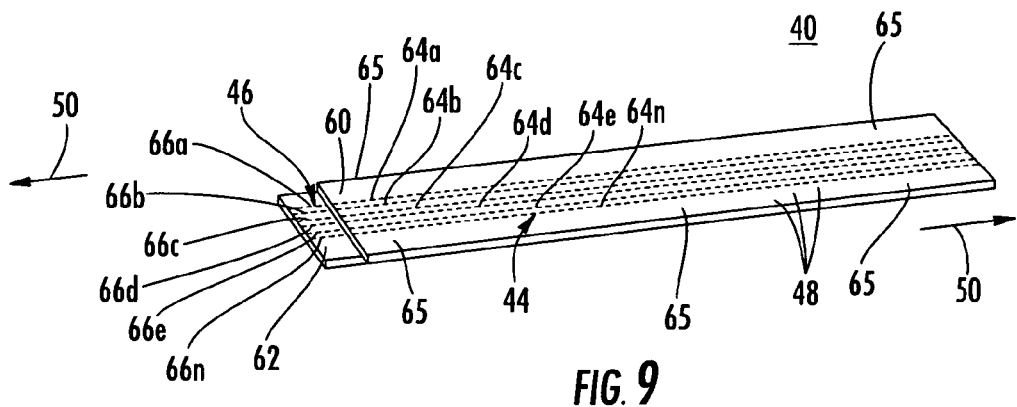
FIG. 9 is an enlarged schematic partial view of another embodiment of the improved respiration monitoring device in accordance with the present invention.

In another embodiment of respiration monitoring device 40, FIG. 9, stretching of the textile occurs out of plane, but capacitance is measured in much the same way, namely, the distance between conductive components or threads changes which is reflected as a change in capacitance. In this embodiment, respiration monitoring device 40 includes elongate stretchable textile members 60 and 62 adjacent each other. Each of elongate stretchable textile members 60 and 62 also include threads 48. Textile member 60 further includes integral woven, knitted or braided conductive component 44 including conductive threads or yarns 64a ... 64n, and textile member 62 includes conductive component 46 including integral woven, knitted or braided conductive threads 66a ... 66n, such that textile member 60 is between conductive threads or yarns 64a ... 64n and 66a ... 66n.

In this configuration, a textile/conductive laminate structure is formed. With conductive threads 64a ... 64n and 66a ... 66n acting as electrodes and textile member 60 as a dielectric, when respiration monitoring device 40 stretches lengthwise as shown at 50, textile member 60 becomes thinner. Therefore, the spacing between conductive threads 64a ... 64n and 66a ... 66n is less, thus changing the capacitance. Elongate stretchable textile members 60 and 62 are preferably connected along stitched regions 65 at predetermined spaced intervals. In this example, the conductive threads which collectively serve as the electrodes also undergo a change in respective electrode area as they are stretched. This effects a change in capacitance in addition to the change in capacitance due to the change caused by the spacing between the conductive threads.

Figure 10A:
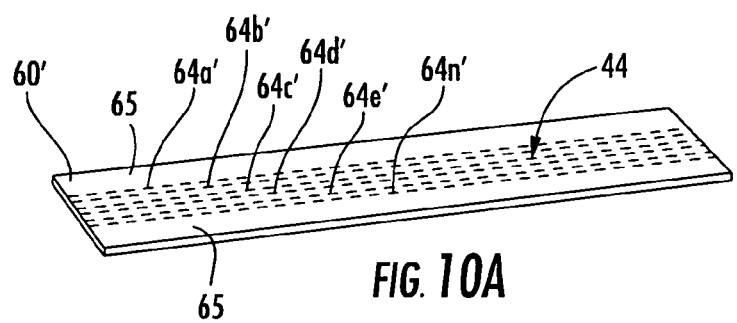
FIGS. 10A and 10B are enlarged schematic partial views of another embodiment of the improved respiration monitoring device in accordance with the present invention.
Figure 10B:
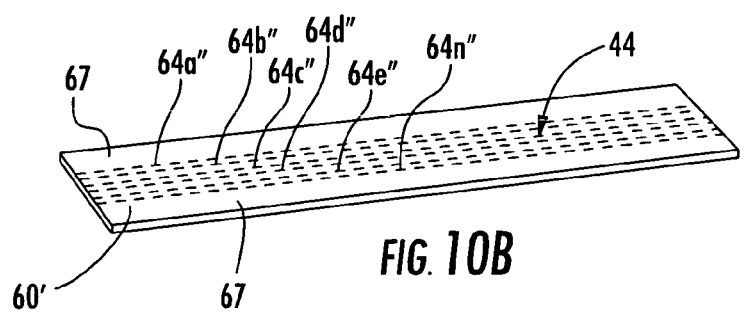

FIGS. 10A and 10B show respiration monitoring device 40 with a single elongate stretchable textile layer or member 60'. In a top view, FIG. 10A, integral woven, knitted or braided conductive component 44 includes conductive threads 64a' ... 64n' on top side 65 of elongate stretchable textile member 60', and conductive threads 64a" ... 64n", FIG. 10B, on bottom side 67 of elongate stretchable textile member 60'. In this single layer or member configuration, respiration monitoring device 40 can be even thinner.

Figure 11:
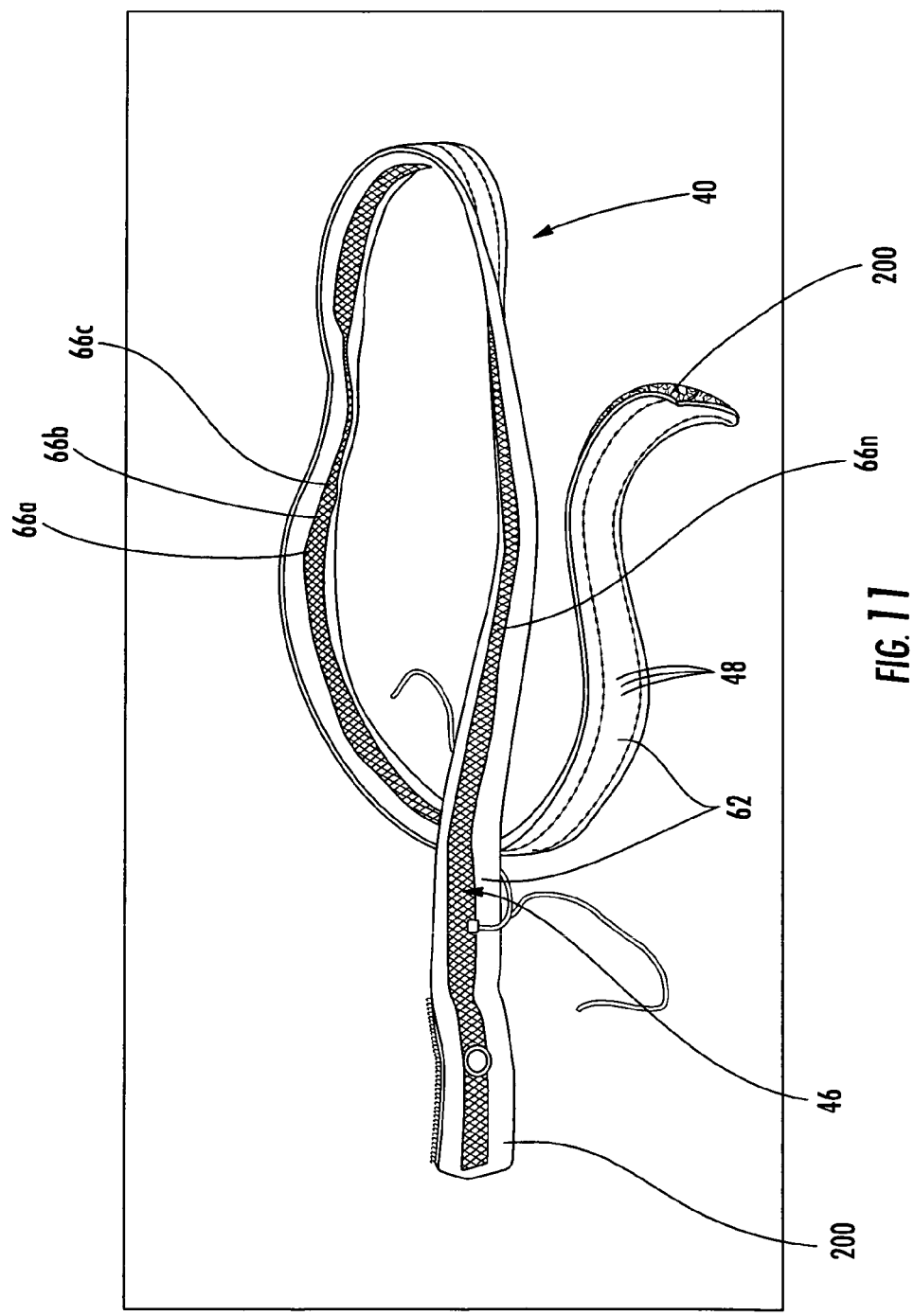
FIG. 11 is a schematic view of the improved respiration monitoring device of FIGS. 10A and 10B.

In any of the foregoing embodiments, respiration monitoring device 40 may be disposed in or on physiological monitoring garment 10, FIG. 6 as an improved respiration sensor 30. Respiration monitoring device 40 may be in or on the garment as shown, or respiration monitoring device 40 may be disposed on elongate stretchable textile data/power bus, and attached by any conventional means. In either case, respiration monitoring device 40 is connected to elongate stretchable textile data/power bus 16. Alternatively, respiration monitoring device 40 may be in the form of a strap. The respiration monitoring device 40 of FIGS. 10A and 10B is shown fully, in strap form, in FIG. 11. In this view, only one conductive component 46 including conductive threads 66a ... 66n and only one textile member 62 are discernible. Fastener 200 such as Velcro at each end of respiration monitoring device 40 holds respiration monitoring device 40 tightly around the subject or patient. To minimize the effects of moisture, respiration monitoring device 40 is typically treated with a moisture-resistant material, or a coating is applied such as fluoropolymer fabric water proofing spray. Other treatments include, for example, incorporation of biocidal materials in order to minimize bacterial growth. Thus, respiration monitoring device 40 provides textile based capacitive sensing in a convenient, comfortable and functional form as a means for sensing respiration rate and type of respiration.

As noted above, other known sensors such as sensor 32, FIG. 6, may also be used with physiological monitoring garment 10. However, a majority of such sensors, i.e. bioelectrode sensors used for bioelectric sensing (e.g., ECG etc.) are conductively coupled, and suffer from a number of disadvantages, such as: extraneous noise induced by contact movement or pressure; base line drift associated with shifts in D.C. levels at the electrode-skin interface, and partial rectification or polarization of the monitored signal. Conductive electrodes are also size-sensitive. Electrode application becomes easier with decreasing size, but since source impedance increases with decreasing size, small electrodes are subject to greater noise. Furthermore, these conventional electrodes are subject to chemical reactions or even drying which can affect signals and tend to cause skin irritation, especially after extended use.

In contrast, capacitively coupled electrodes eliminate any current flow between the skin and the electrode. This decoupling has advantages including: eliminating the possibility for tissue polarization; minimizing sensitivity to chemical reactions; eliminating contact and movement artifacts; minimizing noise sensitivity; and providing an increased level of safety, since electrical problems in the conditioning electronics cannot create a shock to the user. Thus, the advantages of capacitively coupled electrodes over any conductive electrode are clear.

Figure 13:
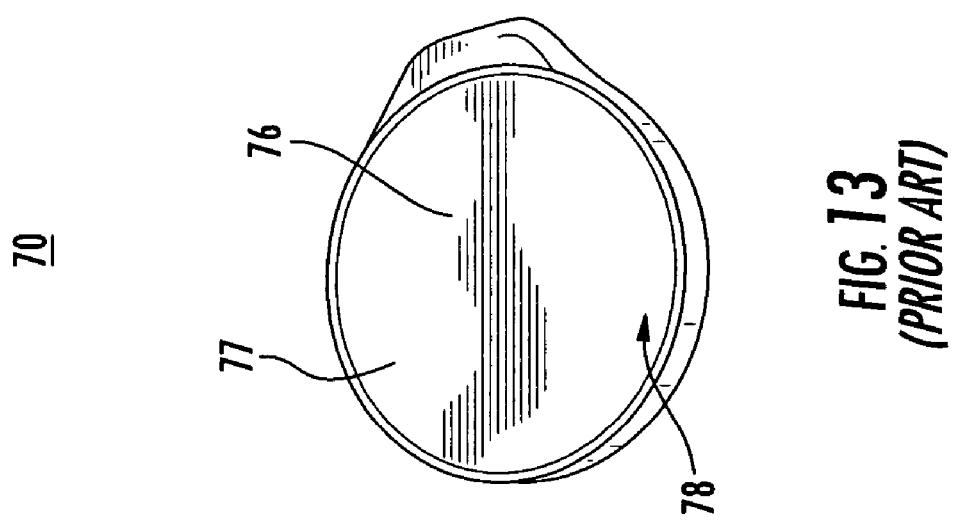
FIG. 13 is a schematic front view of the prior art ECG sensor of FIG. 12.

In one example, sensor 32, FIG. 6, for use with physiological monitoring garment 10 of the subject invention, a conventional bioelectrode sensor 70, FIG. 12, which may be a capacitive electrode such as an electrocardiogram (ECG) sensor. Although an improvement over conductive electrodes, such a conventional prior art sensor 70 typically includes thick rigid plastic housing 72, printed circuit board with conditioning electronics 74, and a stamped metal electrode 76, FIG. 13 which usually includes a thin oxide coating 77 on its front side 78. Even though this form of capacitive electrode does not require complete surface contact with the skin, however, because it is rigid and thick, prior art sensor 70 is prone to bridging, i.e. sensor 70 does not remain in full contact with the patient's skin. Folds of flesh, either fat or muscle, can lift rigid disk sensor 70 on an edge, leading to a complete loss of contact. When bridging occurs, a true signal from sensor 70 is not maintained, resulting in less than accurate readings.

Figure 14:
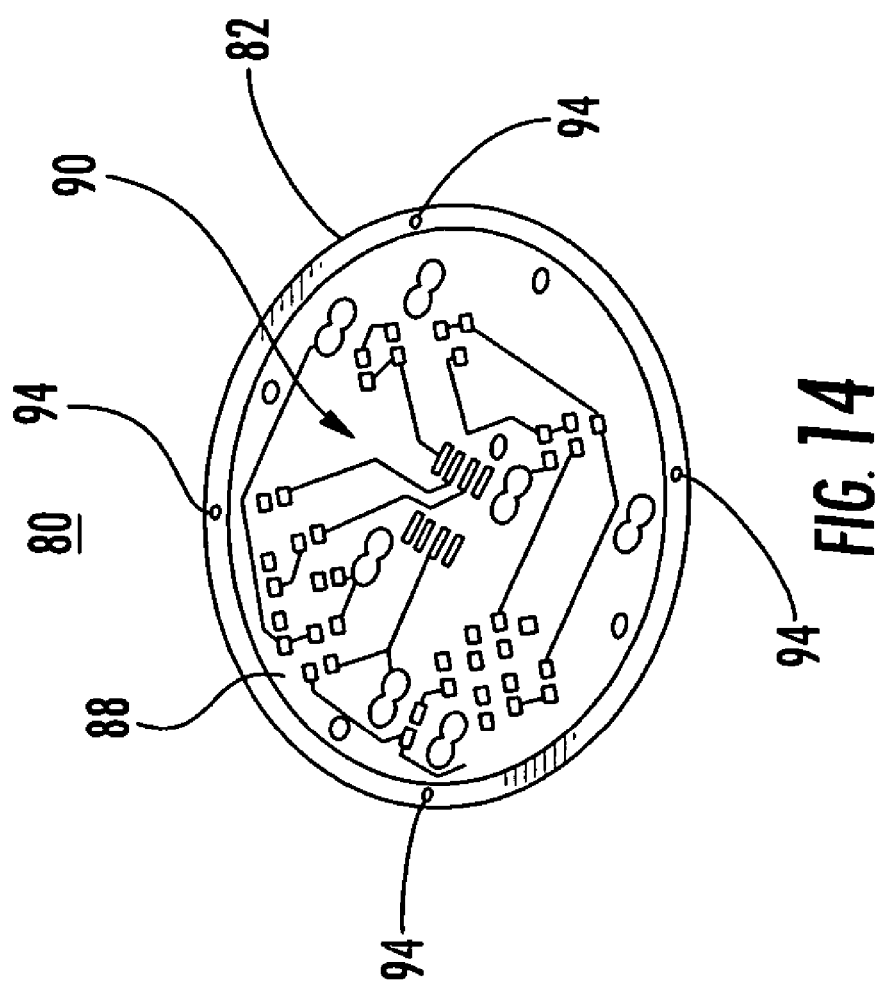
FIG. 14 is a schematic rear view of an improved sensor in accordance with the present invention.

Although such conventional sensors may be used, even with their inherent disadvantages, preferably sensor 32, FIG. 6, for use with physiological monitoring garment 10 of the subject invention is improved sensor 80, FIG. 14. Sensor 80 includes flexible circuit board 82 configured as an electrode, with conductive portion or layer 84, FIG. 15, on one surface 86. Flexible circuit board 82 is preferably comprised of a flexible material such as a liquid crystal polymer or polyesters. Conductive layer or portion 84 can be etched using conventional circuit board fabrication techniques to form specific circuit patterns on the surface. In this way, opposing surface 88, FIG. 14, of flexible circuit board 82 typically includes signal conditioning circuitry 90, although this is not a necessary limitation of the invention as discussed below. Conductive traces 94 interconnect conductive portion 84 with signal conditioning circuitry 90. The flexible nature of circuit board 82 allows the low-profile signal conditioning circuitry 90 to be located with flexible circuit board 82, thus minimizing electrical connections. In one example, conductive portion 84 is a conductive foil laminated on flexible circuit board 82. Conductive portion 84 may also be conductive material that is sputtered or plated on flexible circuit board 82. Thermal lamination or deposition techniques such as vapor deposition may also be utilized to integrate conductive portion 84 onto flexible circuit board 82. Conductive layer or portion 84 may include a thin layer of copper, although the invention is not limited to this material.

Figure 15:
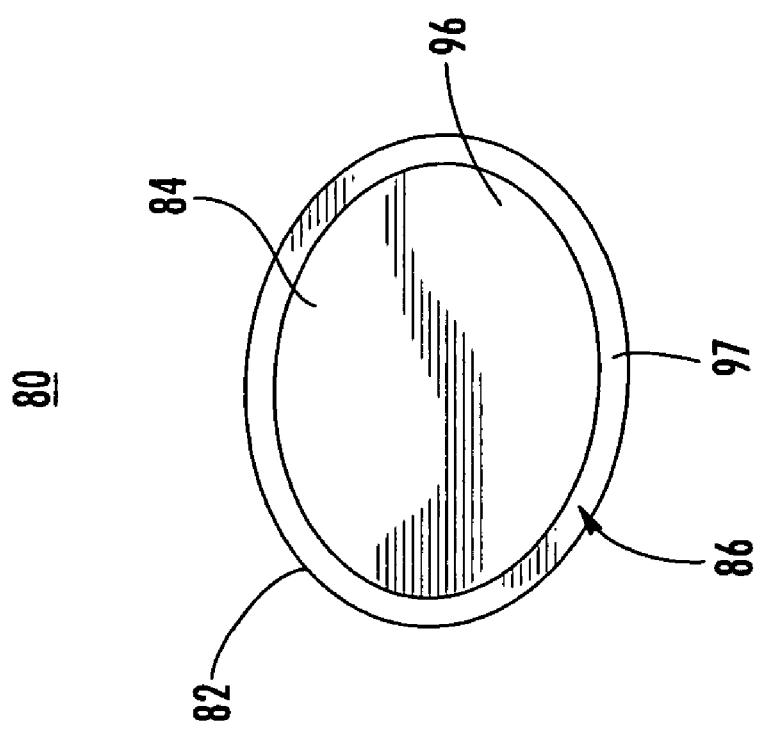
FIG. 15 is a schematic front view of the improved sensor of FIG. 14.

Dielectric material or coating 96, FIG. 15, is disposed on conductive portion 84. In FIG. 15, dielectric material 96 is invisible and covers the entirety of conductive portion 84 and flexible circuit board 82 on this front side. Dielectric material 96 separates flexible circuit board 82, acting as an electrode, from the patient's tissue. As known in the art, changes in biological signals induce a charge in the electrode electrostatically. When dielectric material 96 completely covers conductive portion 84 on the front side of improved sensor 80, it forms insulating edge 97 to prevent short circuiting. Dielectric material 96 may include ceramics or polymers. Dielectric material 96 may include oxides and nitrides such as titanium oxide, silicon oxide or silicon dioxide, titanium oxide or titanium dioxide. Dielectric material 96 may be sputtered, laminated, evaporated, or spun onto conductive portion 84, with a typical thickness of approximately 100 nanometers to 1 micron.

Figure 16A:
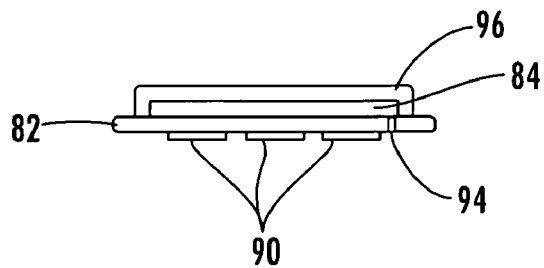
FIGS. 16A-16D are enlarged cross-sectional views of alternative embodiments of the improved sensor of FIG. 14.
Figure 16B:
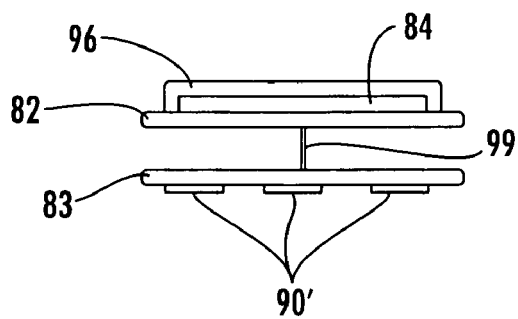
Figure 16C:
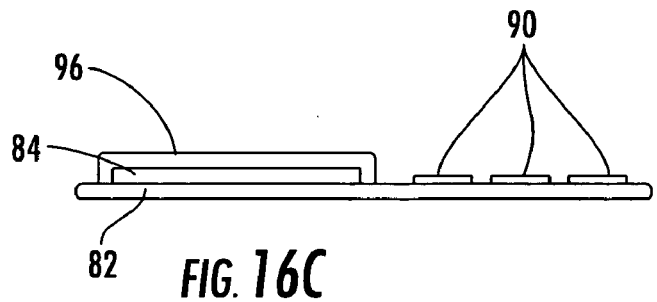
Figure 16D:
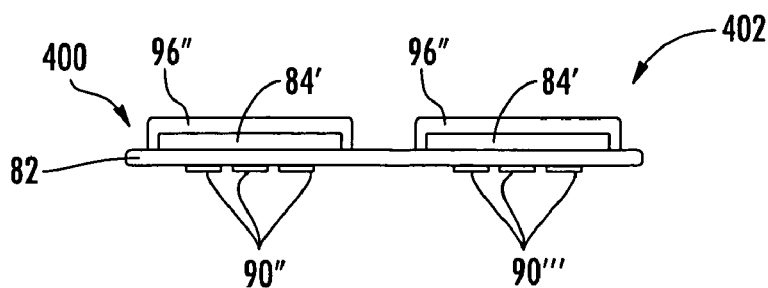

As noted, flexible circuit board 82, FIG. 16A, preferably includes signal conditioning circuitry 90, and conductive traces 94 interconnect conductive portion 84 with signal conditioning circuitry 90. However, signal conditioning circuitry 90', FIG. 16B, may be included on second flexible circuit board 83 connected by wire 99 or other suitable means to flexible circuit board 82, or adjacent conductive portion 84 on flexible circuit board 82, FIG. 16C. In another example, flexible circuit board 82, FIG. 16D, may be configured as at least two electrodes 400, 402 with conductive portions 84' and 84", and dielectric material 96', 96", respectively, and each electrode 400, 402 may include signal conditioning circuitry 90" and 90'''.

Figure 17:
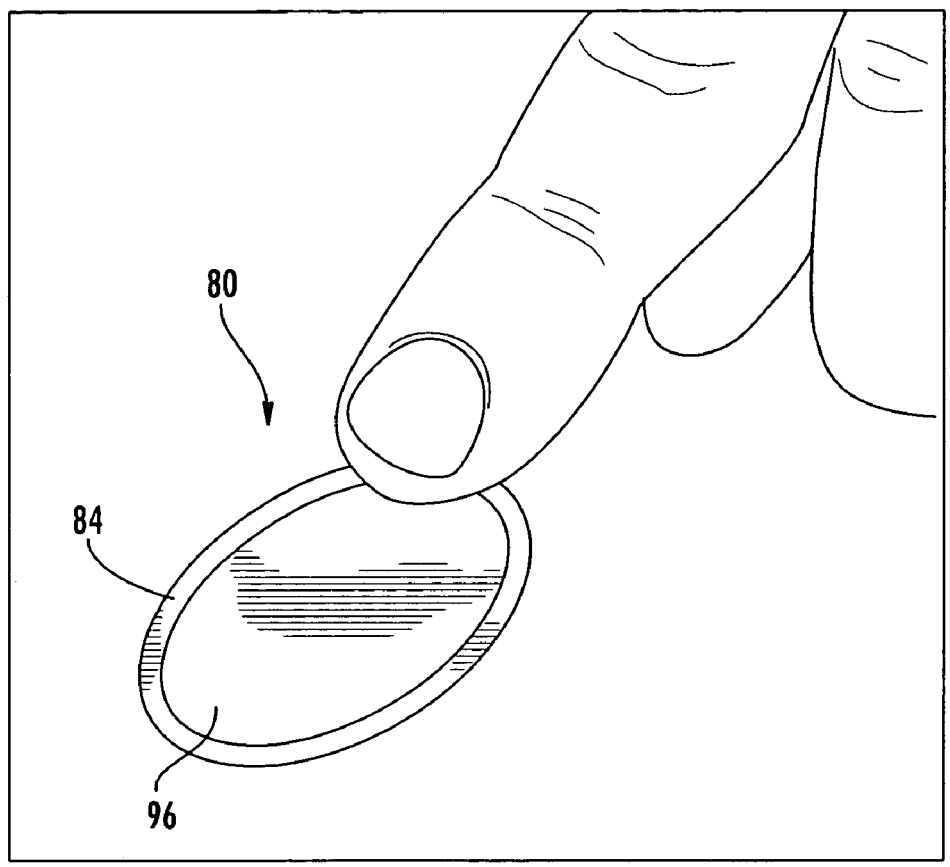
FIG. 17 is a schematic isometric view of the sensor of FIG. 14.

The result is improved sensor 80 which is flexible, thin and low profile, as best shown in FIG. 17. These features make improved sensor 80 more comfortable, and decrease the likelihood of bridging and its effects. Also, with flexible circuit board 82 configured as an electrode and dielectric material disposed on the surface for contact with the patient's skin, sensor 80 acts as a dry capacitive sensor. Thus, the necessity of conductive lubricants or gels, which are required for conventional conductive sensors is eliminated.

Figure 18:
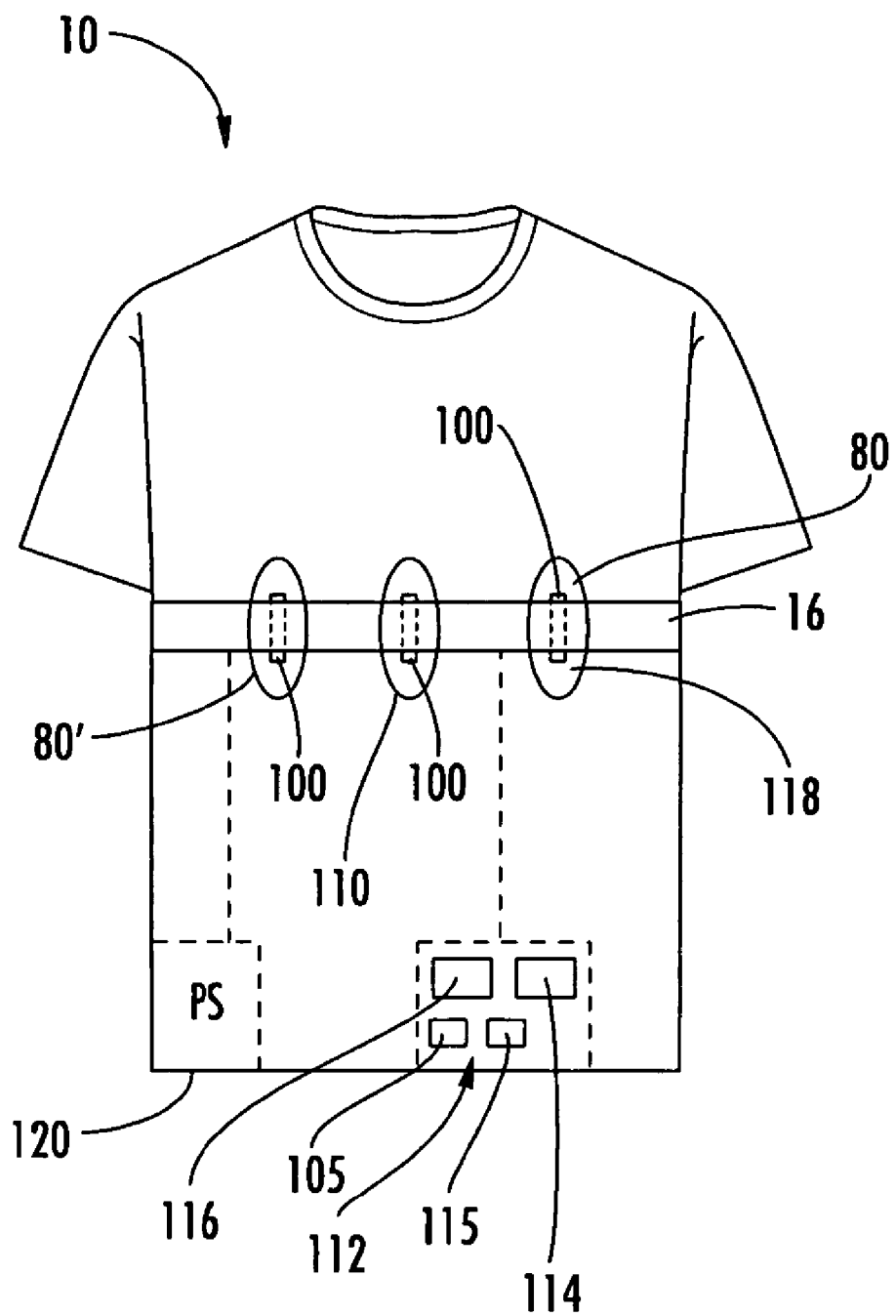
FIG. 18 is a schematic view of the physiological monitoring garment of FIG. 1A including the improved sensor of FIG. 14.

For ECG monitoring, for example, in operation physiological monitoring garment 10, FIG. 18, will typically include two sensors 80 and 80', and may include as many as twelve sensors placed at various locations on the subject or patient as known in the art. In accordance with the present invention, typically one conductive electrode 110 is used as a driven ground to reduce the effects of noise. It is well known that ECG signal strength increases with decreasing distance and orientation to the heart muscle. Thus, when sensor 80 is utilized as an ECG sensor, sensors 80 and 80', are suitably placed on the patient at optimum locations for ECG recording, with locations being known by those skilled in the art. For capacitively coupled electrodes such as improved sensor 80, high impedance buffer electronics 118 will typically be included between sensor 80 and conditioning electronics 105. This is due to the time constant, $\tau$, that exists in the equivalent RC circuit. Heart signal detection requires low frequency response with a large time constant since the events themselves are relatively slow. Furthermore, buffer electronics 118 may act as a transformer to make the signal compatible with conventional monitoring systems, such as conventional ECG monitoring which are typically designed for low source impedance sensors. The signals from buffer electronics 118 can then be fed to the analog-to-digital converter 114 and filters 116 in processing hub 112, which includes microprocessor 115. In accordance with improved sensor 80, buffer electronics 118 are typically included on flexible circuit board 82, FIG. 14. As noted above, however, buffer electronics 118 need not be on flexible circuit board 118 but may be on a second circuit board, for example. Although the operation of sensor 80 has been described as associated with ECG monitoring, sensor 80 may be used for EMG (electromyography) monitoring or EEG (electroencephlograph) monitoring as well.

The physiological monitoring garment of the present invention thus provides a comfortable non-obtrusive, versatile, robust system for monitoring any number of physiological conditions under dynamic conditions and environments, and it does so while the subject or patient remains ambulatory. The garment is useful for ambulatory monitoring, whether in-patient, out-patient, or for non-clinical use, such as athletic performance training, sleep studies, or detection of the onset of sudden infant death syndrome. The inclusion of the stretchable textile data/power bus provides power and data transfer and routing to and from a variety of sensors, which can be attached to or detached from the stretchable textile data/power bus. Thus, the physiological monitoring garment can be washed, without damage to the sensors, and because stretchable textile data/power bus is incorporated into the physiological monitoring garment, it is more comfortable than wiring attached to or surrounding the patient. Also, the improved respiration monitoring device and flexible sensor according to the present invention can be attached or connected to the garment. The respiration monitoring device provides the advantage of added comfort as well as textile based capacitive transduction as a means for sensing respiration. The flexible sensor provides a low profile structure with flexibility to decrease bridging effects and distinct, clear signals for indicating physiological status. By utilizing capacitance, in contrast to conductive systems, there is no direct electrical contact from the patient's skin to the electrode. There is an increased level of safely for the patient or subject, and conductive gels or pastes are not necessary.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A physiological monitoring garment comprising:
   a first fabric portion;
   a second fabric portion;
   an elongate stretchable textile data/power bus between the first fabric portion and the second fabric portion, the elongate stretchable textile data/power bus including a plurality of integral conductors, woven, knitted, or braided along the length thereof in a strain relief pattern;
   a respiration monitoring device connected to said textile data/power bus and including:
      a first elongate stretchable textile member,
      a first conductive component associated with said textile member,
      a second conductive component associated with said textile member, and
      threads of the textile member providing dielectric separation between the first and second conductive components so that the expansion and contraction of said textile member results in a change in the spacing between the first and second conductive components; and
   at least two sensors connected to the textile data/power bus, the sensors each including:
      a flexible circuit board configured as an electrode,
      a conductive portion on one surface of said flexible circuit board, and
      a dielectric material on said conductive portion.

2. A physiological monitoring garment comprising:
   an elastic fabric portion;
   at least one elongate stretchable textile data/power bus disposed on the elastic fabric portion, the elongate stretchable textile data/power bus including a plurality of integral conductors, woven, knitted, or braided along the length thereof in a strain relief pattern;
   a respiration monitoring device connected to said textile data/power bus and including:
      a first elongate stretchable textile member,
      a first conductive component associated with said textile member,
      a second conductive component associated with said textile member, and
      threads of the textile member providing dielectric separation between the first and second conductive components so that the expansion and contraction of said textile member results in a change in the spacing between the first and second conductive components; and
   at least two sensors connected to the textile data/power bus, the sensors each including:
      a flexible circuit board configured as an electrode,
      a conductive portion on one surface of said flexible circuit board, and
      a dielectric material on said conductive portion.

3. A physiological monitoring garment comprising:
   a first fabric portion;
   a second fabric portion;
   an elongate stretchable textile data/power bus between the first fabric portion and the second fabric portion, the elongate stretchable textile data/power bus including a plurality of integral conductors, woven, knitted, or braided along the length thereof in a strain relief pattern; and a respiration monitoring device connected to the data/
power bus and including:
a first elongate stretchable textile member,
a first conductive component associated with said textile
member,
a second conductive component associated with said
textile member, and
threads of the textile member providing dielectric
separation between the first and second conductive
components so that the expansion and contraction
of said textile member results in a change in the
spacing between the first and second conductive
components.

4. The physiological monitoring garment of claim 3 further including at least a third elastic fabric portion and at least a second elongate stretchable textile data/power bus including a plurality of integral conductors, woven, knitted, or braided along the length thereof, and one or more sensors connected to said at least second elongate stretchable textile data/power bus.

5. A physiological monitoring garment comprising:
an elastic fabric portion;
at least one elongate stretchable textile data/power bus
disposed on the elastic fabric portion, the elongate
stretchable textile data/power bus including a plurality
of integral conductors, woven, knitted, or braided along
the length thereof in a strain relief pattern; and
a respiration monitoring device connected to the data/
power bus and including:
a first elongate stretchable textile member,
a first conductive component associated with said textile
member,
a second conductive component associated with said
textile member, and
threads of the textile member providing dielectric
separation between the first and second conductive
components so that the expansion and contraction
of said textile member results in a change in the
spacing between the first and second conductive
components.

6. A respiration monitoring device comprising:
a first elongate stretchable textile member;
a first conductive component associated with said textile
member;
a second conductive component associated with said textile member; and
threads of the textile member providing dielectric separation between the first and second conductive components so that the expansion and contraction of the textile member results in a change in the spacing between the first and second conductive components.

7. The respiration monitoring device of claim 6 in which the first conductive component includes woven, knitted, or braided conductive threads integral with said textile member.

8. The respiration monitoring device of claim 7 in which there are first and second elongate stretchable textile members adjacent each other and each conductive material sputtered or plated on said flexible circuit board.

9. A physiological monitoring garment comprising:
a first elastic fabric portion;
a second elastic fabric portion;
an elongate stretchable textile data/power bus between the
first fabric portion and the second fabric portion, the
elongate stretchable textile data/power bus including a
plurality of integral conductors, woven, knitted, or
braided along the length thereof; and
one or more sensors connected to the elongate stretchable
textile data/power bus, one of said sensors including a
respiration monitoring device, said respiration monitoring device including:
at least a first elongate stretchable textile member,
at least first and second conductive components associated with said textile member, and
threads of said textile member providing dielectric separation between the at least first and second conductive
components so that the expansion and contraction of
the textile member results in a change in the spacing
between the first and second conductive components
for measuring change in capacitance.

10. The physiological monitoring garment of claim 9 in which the first conductive component includes woven, knitted, or braided conductive threads integral with said first textile member.

11. The physiological monitoring garment of claim 10 in which there are a plurality of elongate stretchable textile members adjacent each other and each includes integral woven, knitted, or braided conductive threads.

12. The physiological monitoring garment of claim 9 in which said respiration monitoring device is disposed in or on said garment proximate said data/power bus.

13. A physiological monitoring garment comprising:
a first elastic fabric portion;
a second elastic fabric portion;
an elongate stretchable textile data/power bus between the
first fabric portion and the second fabric portion, the
elongate stretchable textile data/power bus including a
plurality of integral conductors, woven, knitted, or
braided along the length thereof; and
one or more sensors connected to the elongate stretchable
textile data/power bus, one of said sensors including:
a flexible circuit board configured as an electrode in
which an opposing surface of said flexible circuit
board includes signal conditioning circuitry,
a conductive portion on one surface of said flexible
circuit board, and
a dielectric material on said conductive portion.

14. The physiological monitoring garment of claim 13 in which said flexible circuit board is connected to a second flexible circuit board including signal conditioning circuitry.

15. The physiological monitoring garment of claim 13 further including conductive traces interconnecting said conductive portion with said signal conditioning circuitry.

16. The physiological monitoring garment of claim 13 in which the flexible circuit board is configured to include at least two electrodes.

17. The physiological monitoring garment of claim 16 in which the two electrodes each include signal conditioning circuitry.

18. A physiological monitoring garment comprising:
a first elastic fabric portion;
a second elastic fabric portion;
an elongate stretchable textile data/power bus between the
first fabric portion and the second fabric portion, the
elongate stretchable textile data/power bus including a
plurality of integral conductors, woven, knitted, or
braided along the length thereof; and
one or more sensors connected to the elongate stretchable
textile data/power bus in which at least one said sensor
includes:
a flexible circuit board configured to include at least two
electrodes in which the two electrodes each include signal conditioning circuitry, a conductive portion on one surface of said flexible circuit board, and a dielectric material on said conductive portion.

19. A physiological monitoring garment comprising:

an elastic fabric portion;

at least one elongate stretchable textile data/power bus disposed on the elastic fabric portion, the elongate stretchable textile data/power bus including a plurality of integral conductors, woven, knitted, or braided along the length thereof; and one or more sensors connected to the elongate stretchable textile data/power bus, one of said sensors including a respiration monitoring device which includes:

at least a first elongate stretchable textile member, at least first and second conductive components associated with said textile member, and threads of said textile member providing dielectric separation between the at least first and second conductive components so that the expansion and contraction of the textile member results in a change in the spacing between the first and second conductive components for measuring change in capacitance.

20. The physiological monitoring garment of claim 19 in which the first conductive component includes woven, knitted, or braided conductive threads integral with said first textile member.

21. The physiological monitoring garment of claim 20 in which there are a plurality of elongate stretchable textile members adjacent each other and each includes integral woven, knitted, or braided conductive threads.

22. The physiological monitoring garment of claim 19 in which said respiration monitoring device is disposed in or on said garment proximate said data/power bus.

23. A physiological monitoring garment comprising:

an elastic fabric portion;

at least one elongate stretchable textile data/power bus disposed on the elastic fabric portion, the elongate stretchable textile data/power bus including a plurality of integral conductors, woven, knitted, or braided along the length thereof; and one or more sensors connected to the elongate stretchable textile data/power bus, one said sensor including:

a flexible circuit board configured as an electrode in which an opposing surface of said flexible circuit board includes signal conditioning circuitry, a conductive portion on one surface of said flexible circuit board, and a dielectric material on said conductive portion.

24. The physiological monitoring garment of claim 23 in which said flexible circuit board is connected to a second flexible circuit board including signal conditioning circuitry.

25. The physiological monitoring garment of claim 23 further including conductive traces interconnecting said conductive portion with said signal conditioning circuitry.

26. The physiological monitoring garment of claim 23 in which the flexible circuit board is configured to include at least two electrodes.

27. The physiological monitoring garment of claim 26 in which the two electrodes each include signal conditioning circuitry.

28. A physiological monitoring garment comprising:

an elastic fabric portion;

at least one elongate stretchable textile data/power bus disposed on the elastic fabric portion, the elongate stretchable textile data/power bus including a plurality of integral conductors, woven, knitted, or braided along the length thereof; and one or more sensors connected to the elongate stretchable textile data/power bus in which at least one said sensor includes:

a flexible circuit board configured to include at least two electrodes in which the two electrodes each include signal conditioning circuitry, a conductive portion on one surface of said flexible circuit board, and a dielectric material on said conductive portion.

* * * * *